(12) United States Patent
Church et al.

(10) Patent No.: US 10,883,140 B2
(45) Date of Patent: Jan. 5, 2021

(54) METHOD AND SYSTEM OF NANOPORE-BASED INFORMATION ENCODING

(71) Applicant: President and Fellows of Harvard College, Cambridge, MA (US)

(72) Inventors: George M. Church, Brookline, MA (US); Mirkó Palla, Newton, MA (US); Peter Benjamin Stranges, Somerville, MA (US); Jeffrey Matthew Nivala, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 66 days.

(21) Appl. No.: 16/094,526

(22) PCT Filed: Apr. 19, 2017

(86) PCT No.: PCT/US2017/028272
§ 371 (c)(1),
(2) Date: Oct. 18, 2018

(87) PCT Pub. No.: WO2017/184677
PCT Pub. Date: Oct. 26, 2017

(65) Prior Publication Data
US 2019/0136309 A1 May 9, 2019

Related U.S. Application Data

(60) Provisional application No. 62/325,669, filed on Apr. 21, 2016.

(51) Int. Cl.
*C12Q 1/6869* (2018.01)
*C12Q 1/68* (2018.01)

(52) U.S. Cl.
CPC ............. *C12Q 1/6869* (2013.01); *C12Q 1/68* (2013.01)

(58) Field of Classification Search
CPC .................... C12Q 1/6869; G01N 33/48721
See application file for complete search history.

(56) References Cited

U.S. PATENT DOCUMENTS

2010/0035260 A1  2/2010  Olasagasti et al.
2012/0091011 A1  4/2012  Graham et al.
(Continued)

OTHER PUBLICATIONS

Stranges et al, Design and characterization of a nanopore-coupled polymerase for single-molecule DNA sequencing by synthesis on an electrode array (POST ART), 2016, published Oct. 11, 2016, E6749-E6756 (Year: 2016).*

(Continued)

*Primary Examiner* — Narayan K Bhat
(74) *Attorney, Agent, or Firm* — Banner & Witcoff, Ltd.

(57) ABSTRACT

This invention provides methods and systems of DNA synthesis including providing an encoding unit comprising an enzyme, a single-stranded DNA (ssDNA) and a nanopore, providing a lipid bilayer having on opposite sides a cis and a trans reservoir each having a different buffer composition, wherein the nanopore is within the lipid bilayer and the enzyme and the ssDNA are in the cis reservoir, providing an electrode over the lipid bilayer wherein the electrode can modulate voltage across the lipid bilayer, wherein the enzyme catalyzes DNA synthesis in response to the voltage.

22 Claims, 26 Drawing Sheets
Specification includes a Sequence Listing.

(56) References Cited

U.S. PATENT DOCUMENTS

| | | |
|---|---|---|
| 2013/0053544 A1 | 2/2013 | Howarth |
| 2015/0269313 A1 | 9/2015 | Church |
| 2015/0368710 A1* | 12/2015 | Fuller ................ C12Q 1/6874 |
| | | 506/4 |

OTHER PUBLICATIONS

Alseth et al. Inosine in DNA and RNA. Curr Opin Genet Dev Jun. 2014 vol. 26 pp. 116-123. Especially p. 117 fig 1.

Fuller et al. Real-time single-molecule electronic DNA sequencing by synthesis using polymer-tagged nucleotides on a nanopore array. Proc Nat Acad Sci ePub Apr. 18, 2016 vol. 113 No. 19 pp. 5233-5238. Especially Supporting information [online] p. 1 col. 2 para 2.

Nelson et al. phi29 DNA polymerase based rolling circle amplification of templates for DNA sequencing. Biotechniques Jun. 2002 Supplement pp. 44-47. Especially abstract, p. 44 col. 2 para 1, p. 45 col. 1 para 3.

* cited by examiner

FIG. 16

\>ϕ29-SpyCatcher

MASWSHPQFEKGAETHMPRKMYSCDFETTTKVEDCRVWAYGYMNIEDHSEY
KIGNSLDEFMAWVLKVQADLYFHNLKFDGAFIINWLERNGFKWSADGLPNT
YNTIISRMGQWYMIDICLGYKGKRKIHTVIYDSLKKLPFPVKKIAKDFKLT
VLKGDIDYHKERPVGYKITPEEYAYIKNDIQIIAEALLIQFKQGLDRMTAG
SDSLKGFKDIITTKKFKKVFPTLSLGLDKEVRYAYRGGFTWLNDRFKEKEI
GEGMVFDVNSLYPAQMYSRLLPYGEPIVFEGKYVWDEDYPLHIQHIRCEFE
LKEGYIPTIQIKRSRFYKGNEYLKSSGGEIADLWLSNVDLELMKEHYDLYN
VEYISGLKFKATTGLFKDFIDKWTYIKTTSEGAIKQLAKLMLNSLYGKFAS
NPDVTGKVPYLKENGALGFRLGEEETKDPVYTPMGVFITAWARYTTITAAQ
ACYDRIIYCDTDSIHLTGTEIPDVIKDIVDPKKLGYWAHESTFKRAKYLRQ
KTYIQDIYMKEVDGKLVEGSPDDYTDIKFSVKCAGMTDKIKKEVTFENFKV
GFSRKMKPKPVQVPGGVVLVDDTFTIKGSCDYDIPTTENLYFQGAMVDTLS
GLSSEQGQSGDMTIEEDSATHIKFSKRDEDGKELAGATMELRDSSGKTIST
WISDGQVKDFYLYPGKYTFVETAAPDGYEVATAITFTVNEQGQVTVNGKAT
KGDAHI

Color assignment: StrepTag ϕ29 Linker SpyCatcher

\>αHL-SpyTag-His

MADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISDY
YPRNSIDTKEYMSTLTYGFNGNVTGDDTGKIGGLIGANVSIGHTLKYVQPD
FKTILESPTDKKVGWKVIFNNMVNQNWGPYDRDSWNPVYGNQLFMKTRNG
SMKAAENFLDPNKASSLLSSGFSPDFATVITMDRKASKQQTNIDVIYERVR
DDYQLHWTSTNWKGTNTKDKWTDRSSERYKIDWEKEEMTNGGSSGGSSGGAH
IVMVDAYKPTKGHHHHHH

Colors assignment: αHL Linker SpyTag 6xHis

METHOD AND SYSTEM OF NANOPORE-BASED INFORMATION ENCODING

RELATED APPLICATIONS

This application is a National Stage Application under 35 U.S.C. 371 of co-pending PCT application PCT/US17/28272 designating the United States and filed Apr. 19, 2017; which claims the benefit of U.S. provisional application No. 62/325,669 and filed Apr. 21, 2016 each of which are hereby incorporated by reference in their entireties.

STATEMENT OF GOVERNMENT INTERESTS

This invention was made with government support under Grant No. R01HG007415 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 11, 2017, is named 010498_00941-WO_SL.txt and is 12,306 bytes in size.

FIELD

The present invention relates in general to methods of nanopore-based sequencing by synthesis.

BACKGROUND

The information revolution is generating large amounts of complex digital media. This has introduced multiple challenges dealing with archiving, maintenance, and retrieval of information. Nucleic acids such as DNA can be an attractive candidate for long-term information storage because of its high-density encoding capability, optimal archiving conditions, and already established techniques to decode its stored content (Goldman, N. et al. Towards practical, high-capacity, low-maintenance information storage in synthesized DNA. Nature 494, 77-80 (2013)). There remains a need for efficient and accurate nanopore-based information encoding and storage methods and systems.

SUMMARY

The present disclosure addresses this need and is based on the discovery that a scalable, nanopore-based information encoding method using an enzymatic approach can be used for information encoding. The present disclosure provides a method of DNA synthesis including providing an encoding unit including an enzyme, a single-stranded DNA (ssDNA) and a nanopore, providing a lipid bilayer having on opposite sides a first reservoir and a second reservoir, which may be referred to herein as a cis and a trans reservoir respectively, with each reservoir having a different buffer composition, wherein the nanopore provides a channel through the lipid bilayer and may be partially within the lipid bilayer and extending within the lipid bilayer, and the enzyme and the ssDNA are in the first or cis reservoir, and applying a voltage across the lipid bilayer via an electrode wherein the electrode can modulate the voltage across the lipid bilayer to cause migration of or influx of activating ions from the second reservoir through the nanopore and through the lipid membrane and into the first reservoir, and wherein the enzyme is activated in the presence of the activating ions and catalyzes addition of one or more nucleotides present in the first reservoir to the single-stranded DNA.

The disclosure provides a method for making single stranded DNA using a template independent polymerase wherein activating ions are separate from the template independent polymerase, nucleotides and a template strand for extension which are present in a reaction zone. A voltage is used to cause migration of the activating ions into the reaction zone to activate the template independent polymerase to add one or more nucleotides to a terminal end of the template strand. According to one embodiment, a nanopore separates the activating ions from the template independent polymerase, nucleotides and a template strand for extension present in a reaction zone. The nanopore is connected to a lipid bilayer which separates the activating ions from the template independent polymerase, nucleotides and a template strand for extension present in a reaction zone. Applying a voltage across the lipid bilayer causes migration of the activating ions through the nanopore and lipid bilayer and into the reaction zone including the template independent polymerase, nucleotides and a template strand thereby activating the template independent polymerase to add one or more nucleotides to the template strand.

The present disclosure further provides a system of DNA synthesis including an encoding unit comprising an enzyme, a single-stranded DNA (ssDNA) and a nanopore, a lipid bilayer having on opposite sides a cis and a trans reservoir each having a different buffer composition, wherein the nanopore is within the lipid bilayer and the enzyme and the ssDNA are in the cis reservoir, and an electrode that can apply a voltage across the lipid bilayer, wherein the electrode can modulate the voltage across the lipid bilayer, and wherein the enzyme is activated and catalyzes DNA synthesis in response to the voltage.

The present disclosure provides a method of encoding information including providing an encoding unit comprising a terminal deoxynucleotidyl transferase, a single-stranded DNA (ssDNA) and a protein nanopore, providing a lipid bilayer having on opposite sides a cis and a trans reservoir each having a different buffer composition, wherein the protein nanopore is within the lipid bilayer and wherein the terminal deoxynucleotidyl transferase and the ssDNA are in the cis reservoir, providing nucleotide bases to the cis reservoir, and applying a voltage across the lipid bilayer via an electrode wherein the electrode can modulate the voltage across the lipid bilayer, and wherein the information is encoded via terminal deoxynucleotidyl transferase catalyzed nucleotide base addition to the 3' end of the ssDNA in response to the voltage induced ion-flux.

The present disclosure further provides an information encoding system including an encoding unit comprising a terminal deoxynucleotidyl transferase, a single-stranded DNA (ssDNA) and a protein nanopore, a lipid bilayer having on opposite sides a cis and a trans reservoir each having a different buffer composition, wherein the protein nanopore is within the lipid bilayer and wherein the terminal deoxynucleotidyl transferase, the ssDNA and nucleotide bases are in the cis reservoir, and an electrode that can apply a voltage across the lipid bilayer, wherein the electrode can modulate the voltage across the lipid bilayer, and wherein the information is encoded via terminal deoxynucleotidyl transferase catalyzed nucleotide base addition to the 3' end of the ssDNA in response to the voltage induced ion-flux.

The present disclosure provides a method of encoding information including providing an encoding unit including a DNA polymerase, a circular single-stranded DNA (ssDNA) template and a protein nanopore, providing a lipid bilayer having on opposite sides a cis and a trans reservoir each having a different buffer composition, wherein the protein nanopore is within the lipid bilayer and wherein the DNA polymerase and the circular ssDNA template are in the cis reservoir, and applying a voltage across the lipid bilayer via an electrode wherein the electrode can modulate the voltage across the lipid bilayer, and wherein the information is encoded via DNA synthesis in response to the voltage.

The present disclosure further provides an information encoding system including an encoding unit including an enzyme, a single-stranded DNA (ssDNA) and a nanopore, a lipid bilayer having on opposite sides a cis and a trans reservoir each having a different buffer composition, wherein the nanopore is within the lipid bilayer and the enzyme and the ssDNA are in the cis reservoir, and an electrode that can apply a voltage across the lipid bilayer, wherein the electrode can modulate the voltage across the lipid bilayer, wherein the enzyme is activated and catalyzes DNA synthesis in response to the voltage. In one embodiment, the ssDNA is circular.

The present disclosure provides a method of single molecule attachment for high throughput nanopore measurement including providing an encoding unit including a single molecule, a single-stranded DNA (ssDNA) and a nanopore, providing a lipid bilayer having on opposite sides a cis and a trans reservoir each having a different buffer composition, wherein the nanopore is within the lipid bilayer and the single molecule and the ssDNA are in the cis reservoir, and applying a voltage across the lipid bilayer via an electrode wherein the electrode can modulate the voltage across the lipid bilayer, and wherein the single molecule catalyzes DNA synthesis in response to the voltage induced ion-flux.

The present disclosure further provides a system of single molecule attachment for high throughput nanopore measurement including an encoding unit including a single molecule, a single-stranded DNA (ssDNA) and a nanopore, a lipid bilayer having on opposite sides a cis and a trans reservoir each having a different buffer composition, wherein the nanopore is within the lipid bilayer and the single molecule and the ssDNA are in the cis reservoir, and an electrode that can apply a voltage across the lipid bilayer, wherein the electrode can modulate the voltage across the lipid bilayer, and wherein the single molecule catalyzes DNA synthesis in response to the voltage.

The present disclosure provides a composition including an encoding unit comprising a terminal deoxynucleotidyl transferase attached to a protein nanopore, and a lipid bilayer wherein the protein nanopore is within the lipid bilayer.

The present disclosure provides a system including an encoding unit comprising an enzyme, a single-stranded DNA (ssDNA) and a nanopore, and a lipid bilayer having on opposite sides a cis and a trans reservoir each having a different buffer composition, wherein the nanopore is within the lipid bilayer and the enzyme and the ssDNA are in the cis reservoir. In one embodiment, the system further comprises an electrode that can apply a voltage across the lipid bilayer, wherein the electrode can modulate the voltage across the lipid bilayer, wherein the enzyme is activated and catalyzes DNA synthesis in response to the voltage. In another embodiment, the ssDNA is linear or circular.

The present disclosure further provides kits. The kit includes compositions including an encoding unit comprising a terminal deoxynucleotidyl transferase attached to a protein nanopore, and a lipid bilayer wherein the protein nanopore is within the lipid bilayer, and a reagent to reconstitute the terminal deoxynucleotidyl transferase, the nucleotide bases and the ssDNA. Components of a subject kit can be in separate containers; or can be combined in a single container. The kits can further include one or more additional reagents, where such additional reagents can be selected from: a dilution buffer; a reconstitution solution; a wash buffer; a control reagent; a control enzyme; and the like. A subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The present disclosure provides a method of DNA synthesis including applying a voltage across a lipid bilayer having one or more encoding units associated therewith, wherein each encoding unit comprises an enzyme, a single-stranded DNA (ssDNA) and a nanopore, wherein the lipid bilayer has on opposite sides a cis and a trans reservoir each having a different buffer composition, wherein the nanopore is within the lipid bilayer and the enzyme and the ssDNA are conjugated to the nanopore and are in the cis reservoir, and wherein the enzyme is activated and catalyzes DNA synthesis in response to the voltage. In one embodiment, the cis reservoir further comprises nucleotide bases. In another embodiment, the voltage is applied via an electrode that modulates the voltage across the lipid bilayer.

The present disclosure provides a method of encoding information including applying a voltage across a lipid bilayer having one or more encoding units associated therewith, wherein each encoding unit comprises a terminal deoxynucleotidyl transferase, a single-stranded DNA (ssDNA) and a protein nanopore, wherein the lipid bilayer has on opposite sides a cis and a trans reservoir each having a different buffer composition, wherein the protein nanopore is within the lipid bilayer and wherein the terminal deoxynucleotidyl transferase and the ssDNA are conjugated to the nanopore and are in the cis reservoir, and wherein the information is encoded via terminal deoxynucleotidyl transferase catalyzed nucleotide base addition to the 3' end of the ssDNA in response to the voltage induced ion-flux. In one embodiment, the cis reservoir further comprises nucleotide bases. In another embodiment, the voltage is applied via an electrode that modulates the voltage across the lipid bilayer. In one embodiment, the ssDNA is linear.

The present disclosure provides a method of encoding information including applying a voltage across a lipid bilayer having one or more encoding units associated therewith, wherein each encoding unit comprises a DNA polymerase, a circular single-stranded DNA (ssDNA) template and a protein nanopore, wherein the lipid bilayer has on opposite sides a cis and a trans reservoir each having a different buffer composition, wherein the protein nanopore is within the lipid bilayer and wherein the DNA polymerase and the circular ssDNA template are conjugated to the nanopore and are in the cis reservoir, and wherein the information is encoded via DNA synthesis in response to the voltage. In one embodiment, the voltage is applied via an electrode that modulates the voltage across the lipid bilayer. In another embodiment, the cis reservoir contains dATP, dGTP, or dTTP, and wherein the trans reservoir contains dCTP.

The disclosure provides that the enzyme is conjugated to the nanopore or free in the cis reservoir. The disclosure provides that the enzyme is a template dependent or independent DNA polymerase. The disclosure provides that the DNA polymerase is a $\phi$29 DNA polymerase or a terminal deoxynucleotidyl transferase. The disclosure provides that the ssDNA is immobilized to the nanopore. The disclosure provides that the ssDNA is immobilized around the rim of the nanopore at its 5' end. The disclosure provides that the ssDNA is a template or an initiator for DNA synthesis. The disclosure provides that the nanopore is a protein membrane channel. The disclosure provides that the protein membrane channel comprises αHL, MspA, or $\phi$29 connector. The disclosure provides that the cis reservoir contains non-catalytic buffer ($Ca^{2+}$) that prevents base addition during DNA synthesis, and wherein the trans reservoir contains catalytic buffer ($Mg^{2+}/Co^{2+}$) that promotes base addition during DNA synthesis. The disclosure provides that the method and system further includes providing nucleotide bases to the cis reservoir and turning on or otherwise applying the voltage such that catalytic ions ($Mg^{2+}/Co^{2+}$) are injected to the cis side from the trans side, thereby activating the enzyme that catalyzes nucleotide base addition during DNA synthesis. The disclosure provides that the nucleotide bases can be added as a single base or a homopolymer run during DNA synthesis. The disclosure provides that the nucleotide bases comprise dATP, dTTP, dCTP, or dGTP. The disclosure provides that the method and system further includes turning off or discontinuing application of the voltage and flushing the cis reservoir with fresh non-catalytic buffer and removing any nucleotide bases and catalytic ions. The disclosure provides that the method and system is capable of single molecule measurement. The disclosure provides that the terminal deoxynucleotidyl transferase is conjugated to the protein nanopore or free in the cis reservoir.

The disclosure provides that the information is encoded at single-base resolution or homopolymer resolution. The disclosure provides that the information encoding accommodates 12 possible 2-base state transitions. The disclosure provides that the information encoding accommodates N*12 unique N-base state transitions. The disclosure provides that the ssDNA is linear or circular for information encoding or storage. The disclosure provides that the information is encoded and stored in the product DNA. The disclosure provides that the DNA polymerase is conjugated to the protein nanopore or free in the cis reservoir. The disclosure provides that circular ssDNA template is immobilized to the protein nanopore. The disclosure provides that the circular ssDNA template includes cytosine, adenine, thymine, and inosine but not guanine. The disclosure provides that the DNA polymerase is a $\phi$29 DNA polymerase. The disclosure provides that the protein nanopore is a protein membrane channel. The disclosure provides that the cis reservoir contains dATP, dGTP, or dTTP, and wherein the trans reservoir contains dCTP. The disclosure provides that the dCTP flows to the cis reservoir and is incorporated into a complement strand of DNA when the voltage is positive. The disclosure provides that the dATP, dGTP or dTTP is incorporated into a complement strand of DNA when the voltage is negative. The disclosure provides that the method records voltage polarity applied across the lipid bilayer over time by encoding this information into a complement strand of DNA during DNA synthesis. The disclosure provides that the information is stored in the complement strand in the form of regions of bases either containing or lacking cytosine bases at the sites which complement the inosine bases of the template strand, which translates to the "1" or "0" state of a single bit of information. The disclosure provides that the enzyme is conjugated to the nanopore or free in the cis reservoir. The disclosure provides that the nucleotide base can be added as a single base or a homopolymer run during DNA synthesis. The disclosure provides that the system is capable of single molecule measurement. The disclosure provides that the single molecule is a template dependent or independent DNA polymerase. The disclosure provides that the single molecule is conjugated to the nanopore by protein conjugation, such as SpyCatcher/SpyTag protein conjugation. The disclosure provides that the enzyme such as the DNA polymerase is covalently coupled to the α-hemolysin heptamer using protein conjugation, such as a Spy/Catcher/SpyTag conjugation approach. The disclosure provides that the electrode is a complementary metal-oxide-semiconductor (CMOS)-based electrode array for high-throughput electrical recording.

The disclosure provides a composition including an encoding unit comprising a terminal deoxynucleotidyl transferase attached to a protein nanopore, and a lipid bilayer wherein the protein nanopore is within the lipid bilayer. The composition further comprises a single stranded DNA (ssDNA). The disclosure provides that the ssDNA is linear.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Further features and advantages of certain embodiments of the present invention will become more fully apparent in the following description of embodiments and drawings thereof, and from the claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A shows that most DNA polymerases require double-stranded DNA as a substrate, where the 5'→3' strand is used as a primer and the complementary strand 3'→5' is used as a template. FIG. 1B shows that terminal deoxynucleotidyl transferase is capable of catalyzing phosphoryl transfer in the absence of a template that cannot be accommodated in its active site. Adapted from Motea, E. A. & Berdis, A. J. Terminal deoxynucleotidyl transferase: The story of a misguided DNA polymerase. Biochim. Biophys. Acta-Proteins Proteomics 1804, 1151-1166 (2010).

FIG. 2A shows terminal deoxynucleotidyl transferase (TdT) attachment strategy to αHL nanopore via SpyCather-SpyTag conjugation. 5'-immobilized initiator single-stranded DNA strand is also shown, which is being extended by catalysis in the presence of divalent $Mg^{2+}/Co^{2+}$ ion containing buffer. FIG. 2B shows that each monomeric unit can accommodate a TdT enzyme (assembling into a heptameric unit), which can extend each ssDNA tethered to the pore rim with the same information content based on voltage-mediated ion-flux modulation.

FIG. 3A shows to flow in dATP (or other natural nucleotide, one at a time) in non-catalytic buffer ($Ca^{2+}$ or other non-$Mg^{2+}/Co^{2+}$ allowing binding but not covalent bond catalysis). FIG. 3B shows to turn the voltage gradient on across membrane (ON state), such that a plume of catalytic ions ($Mg^{++}/Co^{++}$) is injected to the cis side (from the trans side). Addition of a single base or a homopolymer run to the initiator ssDNA will take place due to catalysis. FIG. 3C shows that if the voltage gradient is not applied (OFF state), catalytic ion migration will not occur, which will lead to no addition of base to ssDNA. FIG. 3D shows to flush cis compartment with fresh non-catalytic buffer to remove any nucleotides and catalytic ion residues. This cycle is repeated with the next nucleotide to be encoded into the ssDNA as desired.

FIG. 4A shows a finite element 2D axisymmetric model of a nanopore surrounded by 1 μm of cis and trans chamber in all directions from the pore. FIGS. 4B-C show the space-dependent concentration of $Ca^{2+}$ ions along the z-axis in the vicinity of the pore, as a function of applied voltage (FIG. 4B, bulk $Ca^{2+}$ concentration in trans is 1 M) or as a function of $Ca^{2+}$ concentration at a fixed applied voltage of 0.3 V (FIG. 4C). Adapted from Anderson, B. N. et al. Probing Solid-State Nanopores with Light for the Detection of Unlabeled Analytes. ACS Nano 8, 11836-11845 (2014).

FIG. 5A shows a schematic of the measurement setup. Both chambers of the experimental cell are equipped with Ag/AgCl electrodes for the electrical recording of the ionic current through the pore. FIG. 5B shows a zoomed-in view of the nanopore area. The optical detection of the ionic current is achieved by adding $Ca^{2+}$ ions to the top (trans) chamber and $Ca^{2+}$ ionophore to the bottom (cis) chamber of the cell. FIG. 5C shows the chemical structure of the ionophore. A voltage across the membrane drives $Ca^{2+}$ ions to the cis side where they complex with the ionophore, resulting in fluorescence signal. The fluorescence intensity is proportional to the $Ca^{2+}$ concentration and, thus, the flow of ions through the pore. Subsequently, a drop in the ionic current during a translocation event can be simultaneously detected from the decrease in the fluorescence intensity FIG. 5D. Adapted from Ivankin, A. et al. Label-Free Optical Detection of Biomolecular Translocation through Nanopore Arrays. ACS Nano 8, 10774-10781 (2014).

FIG. 10 discloses SEQ ID NOS 3, 4, and 5, respectively, in order of appearance.

FIG. 12A shows the protein constructs used to form the porin-polymerase conjugate include unmodified αHL with a Strep-tag, αHL with a C-terminal SpyTag peptide and 6×-His-tag (SEQ ID NO: 1), and φ29 with a C-terminal SpyCatcher domain. Assembly steps are shown in FIG. 12B. αHL-SpyTag-6×-His ("6×-His" disclosed as SEQ ID NO: 1) and unmodified αHL are oligomerized with lipid and the 1:6 SpyTag:unmodified assembled porin is purified. Addition of φ29-SpyCatcher to the 1:6 pore yields one polymerase per αHL pore. A molecular model generated with Rosetta using the determined structures for φ29 polymerase (PDB: 2PYJ), αHL (PDB: 7AHL) and SpyCatcher/SpyTag (PDB: 2X5P) is shown in FIG. 12C. Colors of the proteins match the schematic representations in FIGS. 23A&B. The expected tag exit site on the polymerase and the opening to the nanopore can be in close proximity with distances as short as 46 Å in some models. The stoichiometry in solution of the porin subunits was confirmed by SDS PAGE without boiling. FIG. 12D. To confirm the assembly, excess φ29-SpyCatcher was added to 1:6 pore. The combination yields only pores with one polymerase attached.

FIG. 13A. Attachment of polymerase does not change the mean open channel current. FIG. 13B. The current root-mean-square fluctuation (RMSF) increase in FIG. 13B may be an indication of the polymerase coupled to the pore. When no polymerase is attached to the pore and tagged nucleotide is introduced transient events are observed. FIG. 13C. When polymerase-template is attached to the pore and the complementary base dG6P-dT30 ("dT30" disclosed as SEQ ID NO: 2) is added there are prolonged capture events. FIG. 13D.

FIG. 14A shows current versus dwell time (duration of each current blockade) plots for captures of all tagged nucleotides. Capture events cluster into distinct current and dwell time regions for each tagged-nucleotide. FIG. 14B shows representative single pore traces of tagged-nucleotide capture shown in FIG. 14A. Current blockade levels for each are marked in red. The blockades demonstrate unique, single-molecule events corresponding to the four distinct tag captures.

FIG. 15B also discloses SEQ ID NO: 8. (See, e.g., WO2013191793 for general descriptions of real-time detection of successive tagged nucleotide incorporations into a DNA template catalyzed by nanopore-bound polymerase on the chip.)

FIG. 16 shows sequences of φ29 (SEQ ID NO: 9) and αHL (SEQ ID NO: 10) constructs with colored annotations for the various protein sequence regions. FIG. 16 also discloses SEQ ID NO: 1.

DETAILED DESCRIPTION

Figure 1A:
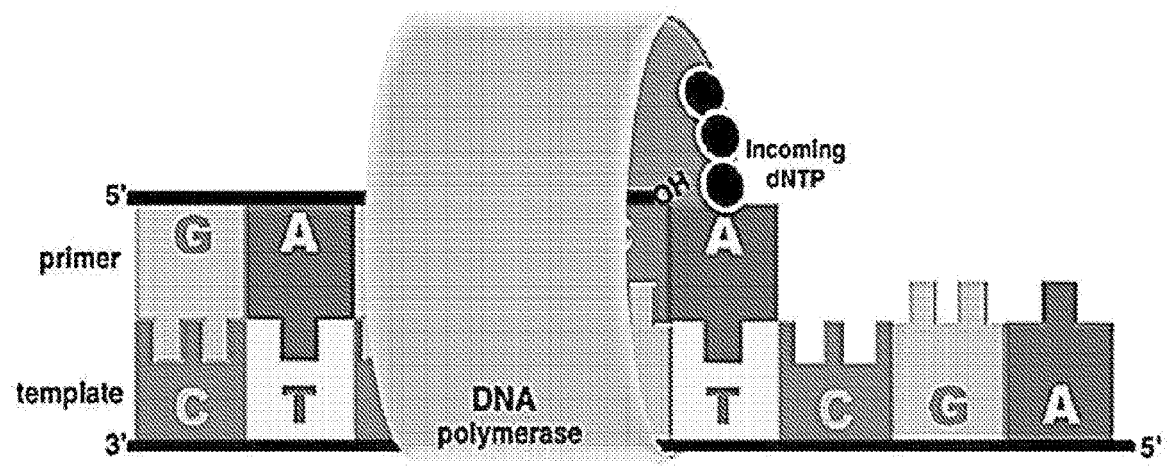
FIGS. 1A-B depict simplified models for template-dependent and template-independent DNA polymerase activity.

The present disclosure provides a nanopore-based information encoding method using an enzymatic approach for various applications. According to one aspect, the disclosure provides a method of nucleic acid synthesis including applying a voltage to cause migration of activating ions from a first location to a reaction zone including a template independent polymerase, nucleotides and an initiator strand including a terminal nucleotide, wherein the activating ions activate the template independent polymerase to add one or more nucleotides to the terminal nucleotides of the initiator strand. In one embodiment, the template independent polymerase and the initiator are co-localized on a substrate. In one embodiment, the reaction zone is separated from the first location by a nanopore or nanochannel under influence of an electric field. In another embodiment, the reaction zone is separated from the first location by a nanopore or nanochannel having a portion of the nanopore or nanochannel within a lipid bilayer under influence of an electric field. In one embodiment, the reaction zone is separated from the first location by a nanopore or nanochannel having a portion of the nanopore or nanochannel within a lipid bilayer under influence of an electric field, and wherein application of the electric field causes migration of the activating ions from the first location through the nanopore or nanochannel and into the reaction zone wherein the template independent polymerase is activated to add one or more nucleotides to the terminal nucleotide of the initiator strand.

According to certain aspects, the present disclosure provides methods and systems of DNA synthesis. The methods of DNA synthesis include providing an encoding unit including an enzyme, a single-stranded DNA (ssDNA) and a nanopore, providing a lipid bilayer having on opposite sides a cis and a trans reservoir each having a different buffer composition, wherein the nanopore is within the lipid bilayer and the enzyme and the ssDNA are in the cis reservoir, and applying a voltage across the lipid bilayer via an electrode wherein the electrode can modulate the voltage across the lipid bilayer, and wherein the enzyme is activated and catalyzes DNA synthesis in response to the voltage. In some embodiments, the enzyme can be conjugated to the nanopore or in the cis reservoir. In some embodiments, the lipid bilayer has two reservoirs on either side such that each reservoir contains a different composition of various types of buffer, salt, or concentrations known to a skilled in the art. In one embodiment, the cis reservoir contains non-catalytic buffer ($Ca^{2+}$) that prevents base addition during DNA synthesis, and wherein the trans reservoir contains catalytic buffer ($Mg^{2+}/Co^{2+}$) that promotes base addition during DNA synthesis. In another embodiment, nucleotide bases are provided to the cis reservoir and the voltage is turned on such that catalytic ions ($Mg^{2+}/Co^{2+}$) are injected to the cis side from the trans side, thereby activating the enzyme that catalyzes nucleotide base addition during DNA synthesis.

According to certain other aspects, the present disclosure provides methods and systems of encoding information. The methods of information encoding include providing an encoding unit comprising a terminal deoxynucleotidyl transferase, a single-stranded DNA (ssDNA) and a protein nanopore, providing a lipid bilayer having on opposite sides a cis and a trans reservoir each having a different buffer composition, wherein the protein nanopore is within the lipid bilayer and wherein the terminal deoxynucleotidyl transferase and the ssDNA are in the cis reservoir, providing nucleotide bases to the cis reservoir, and applying a voltage across the lipid bilayer via an electrode wherein the electrode can modulate the voltage across the lipid bilayer, and wherein the information is encoded via terminal deoxynucleotidyl transferase catalyzed nucleotide base addition to the 3' end of the ssDNA in response to the voltage induced ion-flux. In one embodiment, the cis reservoir contains non-catalytic buffer ($Ca^{2+}$) that prevents base addition, and the trans reservoir contains catalytic buffer ($Mg^{2+}/Co^{2+}$) that promotes base addition. In another embodiment, the terminal deoxynucleotidyl transferase is activated by catalytic ions ($Mg^{2+}/Co^{2+}$) that are injected to the cis side from the trans side when the voltage is turned on and catalyzes the addition of the nucleotide base to the ssDNA. In one embodiment, the methods include providing an encoding unit comprising a DNA polymerase, a circular single-stranded DNA (ssDNA) template and a protein nanopore, providing a lipid bilayer having on opposite sides a cis and a trans reservoir each having a different buffer composition, wherein the protein nanopore is within the lipid bilayer and wherein the DNA polymerase and the circular ssDNA template are in the cis reservoir, and applying a voltage across the lipid bilayer via an electrode wherein the electrode can modulate the voltage across the lipid bilayer, and wherein the information is encoded via DNA synthesis in response to the voltage. In one embodiment, the cis reservoir contains dATP, dGTP, or dTTP, and the trans reservoir contains dCTP. In one embodiment, the dCTP flows to the cis reservoir and is incorporated into a complement strand of DNA when the voltage is positive. In one embodiment, the dATP, dGTP or dTTP is incorporated into a complement strand of DNA when the voltage is negative. In certain embodiments, the methods and systems can record voltage polarity applied across the lipid bilayer over time by encoding this information into a complement strand of DNA during DNA synthesis. In certain embodiments, the methods and systems of nucleic acid synthesis or information encoding are used in a microfluidic system wherein the cis or trans buffering reservoir corresponds to microfluidic chamber of the microfluidic system and wherein the activating or inactivating ions and nucleotide bases are flowed to the corresponding microfluidic chamber.

According to certain aspects, a composition is provided that comprises an encoding unit comprising a terminal deoxynucleotidyl transferase attached to a protein nanopore, and a lipid bilayer wherein the protein nanopore is within the lipid bilayer. In one embodiment, the composition further comprises a single stranded DNA (ssDNA). In one embodiment, the lipid bilayer has on opposite sides a cis and a trans reservoir each having a different buffer composition, and the terminal deoxynucleotidyl transferase, the ssDNA and nucleotide bases are in the cis reservoir. In one embodiment, an electrode can apply a voltage across the lipid bilayer, wherein the electrode can modulate the voltage across the lipid bilayer, and wherein the terminal deoxynucleotidyl transferase catalyzes nucleotide base addition to the 3' end of the ssDNA in response to the voltage induced ion-flux. In some embodiments, the terminal deoxynucleotidyl transferase is conjugated to the protein nanopore or free in the cis reservoir. In some embodiments, multiple terminal deoxynucleotidyl transferase molecules are tethered to one or more nanopore subunits.

The term "nanopore," as used herein, generally refers to a pore, nanopore sensor, nanogap, nanochannel, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore. Exemplary nanopores include a hole or passage through a membrane formed by a multimeric protein ring. Typically, the passage is 0.2-25 nm wide. Nanopores, as used herein, may include transmembrane structures that may permit the passage of molecules through a membrane. Examples of nanopores include α-hemolysin (*Staphylococcus aureus*) and MspA (*Mycobacterium smegmatis*). Other examples of nanopores may be found in the art describing nanopore sequencing or described in the art as pore-forming toxins, such as the β-PFTs Panton-Valentine leukocidin S, aerolysin, and Clostridial Epsilon-toxin, the α-PFTs cytolysin A, the binary PFT anthrax toxin, or others such as pneumolysin or gramicidin. Nanopores have become technologically and economically significant with the advent of nanopore sequencing technology. Methods for nanopore sequencing are known in the art, for example, as described in U.S. Pat. No. 5,795,782, which is incorporated by reference. Briefly, nanopore detection involves a nanopore-perforated membrane immersed in a voltage-conducting fluid, such as an ionic solution including, for example, KCl, NaCl, NiCl, LiCl or other ion forming inorganic compounds known to those of skill in the art. A voltage is applied across the membrane, and an electric current results from the conduction of ions through the nanopore. When the nanopore interacts with polymers, such as DNA, flow through the nanopore is modulated in a monomer-specific manner, resulting in a change in the current that permits identification of the monomer(s). Nanopores within the scope of the present disclosure include solid state nonprotein nanopores known to those of skill in the art and DNA origami nanopores known to those of skill in the art. Such nanopores provide a nanopore width larger than known protein nanopores which allow the passage of larger molecules for detection, while still being sensitive enough to detect a change in ionic current when the complex passes through the nanopore.

The term "nucleic acid," as used herein, generally refers to a molecule comprising one or more nucleic acid subunits. A nucleic acid may include one or more subunits selected from adenosine (A), cytosine (C), guanine (G), thymine (T), uracil (U) and inosine (I), or modification and variants thereof. A nucleotide can include A, C, G, T, U or I, or variants thereof. A nucleotide can include any subunit that can be incorporated into a growing nucleic acid strand. In some examples, a nucleic acid is deoxyribonucleic acid (DNA) or ribonucleic acid (RNA), or derivatives thereof. A nucleic acid may be single-stranded or double stranded. Nucleic acid molecules may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The term "polymerase," as used herein, generally refers to any enzyme capable of catalyzing a polymerization reaction, and variants, mutants, or homologues thereof. Examples of polymerases include, without limitation, a DNA or RNA polymerase, a terminal deoxynucleotidyl transferase (TdT), a transcriptase or a ligase, and variants, mutants, or homologues thereof. A polymerase can be a polymerization enzyme. In certain embodiments, the enzymes capable of catalyzing a polymerization reaction include template-dependent or template-independent polymerases. In exemplary embodiments, suitable template-independent polymerase includes a terminal deoxynucleotidyl transferase (TdT), and variants, mutants, or homologues thereof. In certain exemplary embodiments, mutant TdTs having mutation residues introduced in the enzyme's catalytic sites can be used. In certain other embodiments, a single-stranded DNA binding protein (SSB) and TdT (SSB-TdT) fusion protein having improved processivity can be used. In the SSB-TdT fusion protein, the SSB portion binds with high affinity in a cooperative manner to the single-stranded DNA while the TdT portion of the fusion protein retains the processivity and catalyzes continuous nucleotide base addition to the 3' end of the initiator ssDNA, thus enhancing gene synthesis. In certain other embodiments, suitable template-dependent polymerases include any strand displacing DNA polymerase, such as φ29 and Bst (full length or large fragment), and variants, mutants, or homologues thereof. In some embodiments, these template-dependent polymerases include mutations at single or multiple residue sites to improve processivity, similar to TdT mutants via protein engineering. Selection of suitable DNA polymerases are known to a skilled in the art and are available in various commercial sources such as in the tools and resources section of the website of New England Biolabs, Inc.

Nanopore-Based Ion-Flux Modulator Methods and Systems

Described herein are methods, devices and systems for information encoding (or DNA synthesis) using, or with the aid of, one or more nanopores. The one or more nanopores may be inserted in a membrane (e.g., lipid bi-layer) that is disposed adjacent or in sensing proximity to an electrode that is part of, or coupled to, an integrated circuit.

In certain examples, a nanopore device includes a single nanopore in a membrane that is adjacent or sensing proximity to an electrode. In other examples, a nanopore device includes at least 1, 2, 3, 4, 5, 6, 7, 8, 9, 10, 20, 30, 40, 50, 60, 70, 80, 90, 100, 1000, or 10,000 nanopores in proximity to a sensor circuit or sensing electrodes. The one or more nanopore may be associated with an individual electrode and sensing integrated circuit or a plurality of electrodes and sensing integrated circuits.

A nanopore-based ion-flux modulator system may include a reaction chamber that includes one or more nanopore devices. A nanopore device may be an individually addressable nanopore device (e.g., a device that is capable of detecting a signal and providing an output independent of other nanopore devices in the system). An individually addressable nanopore can be individually readable. In some cases, an individually addressable nanopore can be individually writable. As an alternative, an individually addressable nanopore can be individually readable and individually writable. The system can include one or more computer processors for facilitating sample preparation and various operations of the disclosure, such as nucleic acid synthesis. The processor can be coupled to nanopore device.

A nanopore device may include a plurality of individually addressable sensing electrodes. Each sensing electrode can include a membrane adjacent to the electrode, and one or more nanopores in the membrane. A plurality of nanopore devices may be arranged in an array.

An enzyme (e.g., DNA polymerase, RNA polymerase, ligase) may incorporate nucleotides to a growing polynucleotide chain. Enzymes (e.g., polymerases) provided herein can generate polymer chains.

Figure 1B:
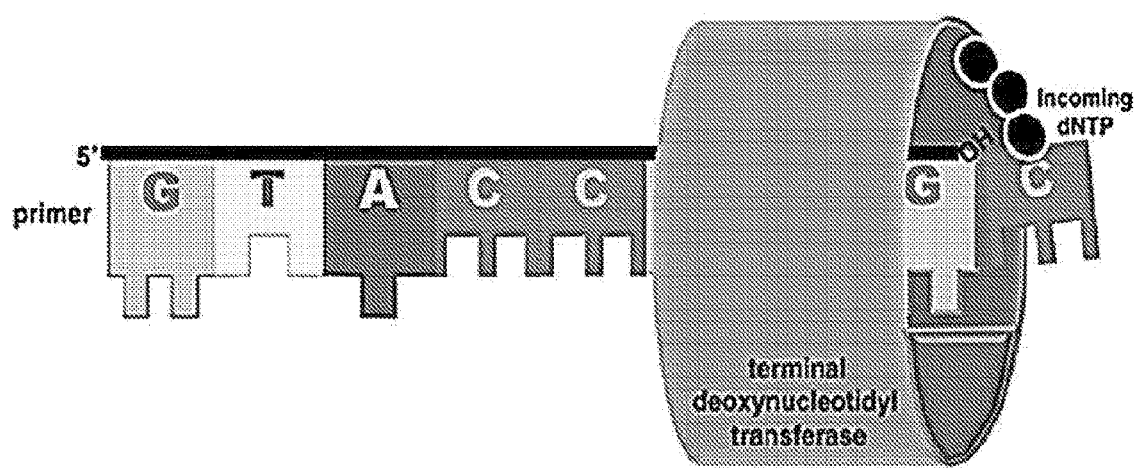

FIGS. 1A-B schematically depict simplified models for template-dependent and template-independent DNA polymerase activity. In the template dependent mode, incoming dNTPs are incorporated into the growing strand that is complementary to the template strand. In the template independent mode, template independent polymerase such as a terminal deoxynucleotidyl transferase catalyzes phosphoryl transfer in the absence of a template.

The present disclosure provides methods and systems for nucleic acid sequencing by synthesis with the aid of a nanopore. The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

In some cases, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid. The tag may remain attached to the nucleotide. Tags for nucleotides are known to a skilled in the art. For example, tags are described in US Patent Application No. 2014/0134616, which is hereby incorporated by reference in its entirety. A detected signal may be collected and stored in a memory location, and later used to construct a sequence of the nucleic acid. The collected signal may be processed to account for any abnormalities in the detected signal, such as errors. FIGS. 2-6 show various examples and schematics of the nanopore-based nucleic acid sequencing by synthesis.

The present disclosure provides enzymes e.g., a DNA or RNA polymerase, a transcriptase or a ligase in the nanopore-based nucleic acid sequencing by synthesis with the tagged nucleotides as described herein. In some cases, the enzyme is any enzyme that creates a nucleic acid strand by phosphate linkage of nucleotides. In some cases, the DNA polymerase is 9° N polymerase or a variant thereof, E. Coli DNA polymerase I, Bacteriophage T4 DNA polymerase, Sequenase, Taq DNA polymerase, 9° N polymerase (exo-)A485L/Y409V, phi29 DNA Polymerase (φ29 DNA Polymerase), Bst polymerase, or variants, mutants, or homologues thereof. A homologue can have any suitable percentage homology, including without limitation at least about 30%, at least about 40%, at least about 50%, at least about 60%, at least about 70%, at least about 80%, at least about 90%, or at least about 95% sequence identity.

The polymerase can have kinetic rate profile that is suitable for detection of the tags by the nanopore. The rate profile can refer to the overall rate of nucleotide incorporation and/or a rate of any step of nucleotide incorporation such as nucleotide addition, enzymatic isomerization such as to or from a closed state, cofactor binding or release, product release, incorporation of nucleic acid into the growing nucleic acid, or translocation.

The kinetics of the enzyme can also be affected and/or controlled by manipulating the composition of the buffer in contact with the enzyme. For example, non-catalytic divalent ions (e.g., ions that do not promote polymerase function such as $Ca^{2+}$) can be mixed with catalytic divalent ions (e.g., ions that promote polymerase function such as $Mg^{2+}$/or $Co^{2+}$) to stop or slow the polymerase down. The buffer conditions that promote the TdT polymerase function are well established in the art and are known to a skilled in the art. In certain exemplary embodiments, the reaction condition that promotes the TdT polymerase function is described according to the commercial vendor (NEB) in the typical DNA tailing reaction (continuous ssDNA extension) as follows:

Step 1. Mix:
 a. 5.0 µl 10×TdT Buffer
 b. 5.0 µl 2.5 mM $CoCl_2$ solution provided c. 5.0 pmols DNA (330 ng for 100 bp, 1 μg for 300 bp, 10 pmols DNA ends)

d. 0.5 μl 10 mM dNTP (alpha-32P dATP may also be used)

e. 0.5 μl Terminal Transferase (20 units/μl) deionized H$_2$O to a final volume of 50 μl.

Step 2. Incubate at 37° C. for 30 minutes, where 1× Terminal Transferase Reaction Buffer is as follows:

50 mM Potassium Acetate
20 mM Tris-acetate
10 mM Magnesium Acetate
pH 7.9@25° C.

A skilled in the art can optimize and adjust the reaction condition for optimum result.

The disclosure provides that an enzyme may be attached to the nanopore. Suitable methods for attaching the enzyme to the nanopore include cross-linking such as the formation of intra-molecular disulfide bonds. The nanopore and the enzyme may also be a fusion protein (i.e., encoded by a single polypeptide chain). Methods for producing fusion proteins may include fusing the coding sequence for the enzyme in frame and adjacent to the coding sequence for the nanopore (without a stop codon in between) and expressing this fusion sequence from a single promoter. In some examples, the enzyme may be attached or otherwise coupled to the nanopore using molecular staples or protein fingers. In some cases, the enzyme is attached through an intermediate molecule or linker, such as for example biotin conjugated to both the enzyme and the nanopore with streptavidin tetramers linked to both biotins. The enzyme can also be attached to the nanopore with an antibody. In some cases, proteins that form a covalent bond between each other (e.g., the SpyTag™/SpyCatcher™ system) are used to attach the polymerase to the nanopore. In some cases, phosphatase enzymes or an enzyme that cleaves the tag from the nucleotide are also attached to the nanopore. FIGS. 12A-D show schematics of an embodiment of the conjugation strategy wherein an amide bond is formed between Lys and Asp side chains via SpyCatcher—SpyTag.

Tags of the disclosure may be atoms or molecules, or a collection of atoms or molecules. A tag may provide an optical, electrochemical, magnetic, or electrostatic (e.g., inductive, capacitive) signature, which signature may be detected with the aid of a nanopore. A nucleotide can include a tag (or tag species) that is coupled to any location of the nucleotide including, but not limited to a phosphate (e.g., gamma phosphate), sugar or nitrogenous base moiety of the nucleotide. In some cases, tags are detected while tags are associated with a polymerase during the incorporation of nucleotide tags. In some examples, the tag can move through or in proximity to the nanopore and be detected with the aid of the nanopore.

The present disclosure provides a method for sequencing a nucleic acid. The method comprises incorporating (e.g., polymerizing) tagged nucleotides. In some cases, a tag associated with an individual nucleotide can be detected by a nanopore without being released from the nucleotide upon incorporation.

The present disclosure provides a chip for a nanopore-based nucleic acid sequencing by synthesis that can comprise a plurality of individually addressable nanopores. An individually addressable nanopore of the plurality can contain at least one nanopore formed in a membrane disposed adjacent to an integrated circuit. Each individually addressable nanopore can be capable of detecting a tag associated with an individual nucleotide. The nucleotide can be incorporated (e.g., polymerized) and the tag may not be released from the nucleotide upon incorporation.

The following examples are set forth as being representative of the present disclosure. These examples are not to be construed as limiting the scope of the present disclosure as these and other equivalent embodiments will be apparent in view of the present disclosure, figures and accompanying claims.

Example I

Nanopore-based ion-flux Modulator for Enzymatic Information Encoding
Components:

Almost every polymerase known to date uses a DNA or RNA template to catalytically incorporate a mononucleotide into the growing primer strand. Terminal deoxynucleotidyl transferase (TdT), however is a unique DNA polymerase, which performs template-independent DNA synthesis using a single-stranded DNA (ssDNA) as the substrate (Motea, E. A. & Berdis, A. J. Terminal deoxynucleotidyl transferase: The story of a misguided DNA polymerase. Biochim. Biophys. Acta-Proteins Proteomics 1804, 1151-1166 (2010)). (FIGS. 1A-B). In vitro studies showed that TdT can incorporate all four natural nucleotides into a ssDNA (Kato, K. I., Goncalves, J. M., Houts, G. E. & Bollum, F. J. Deoxynucleotide-polymerizing enzymes of calf thymus gland. II. Properties of the terminal deoxynucleotidyltransferase. J. Biol. Chem. 242, 2780-2789 (1967)). Subsequent studies also confirmed that TdT requires an initiator chain at least six nucleotides in length (Chang, L. M., Cassani, G. R. & Bollum, F. J. Deoxynucleotide-polymerizing enzymes of calf thymus gland. VII. Replication of homopolymers. J. Biol. Chem. 247, 7718-7723 (1972)). As all polymerases, TdT requires a divalent metal ion to catalyze the phosphoryl transfer reaction to incorporate a nucleotide into a growing DNA strand. It has been shown that $Mg^{2+}$ facilitates dGTP/dATP, while $Co^{2+}$ increases dCTP/dTTP catalytic polymerization efficiency (Chang, L. M. & Bollum, F. J. Multiple roles of divalent cation in the terminal deoxynucleotidyl-transferase reaction. J. Biol. Chem. 265, 17436-17440 (1990)). TdT catalytic activity has been shown to be regulated by protein-protein interactions. For example, TdT interacting factor (TdiFs) binds to the C-terminus of TdT and increases its polymerase activity by 4-fold (Fujita, K. et al. Terminal deoxynucleotidyltransferase forms a ternary complex with a novel chromatin remodeling protein with 82 kDa and core histone. Genes Cells 8, 559-571 (2003)). Thus, primer length, divalent metal ion and protein-protein interactions ("optimization or control" parameters) are critical regulating the catalytic activity of TdT in general.

Figure 2A:
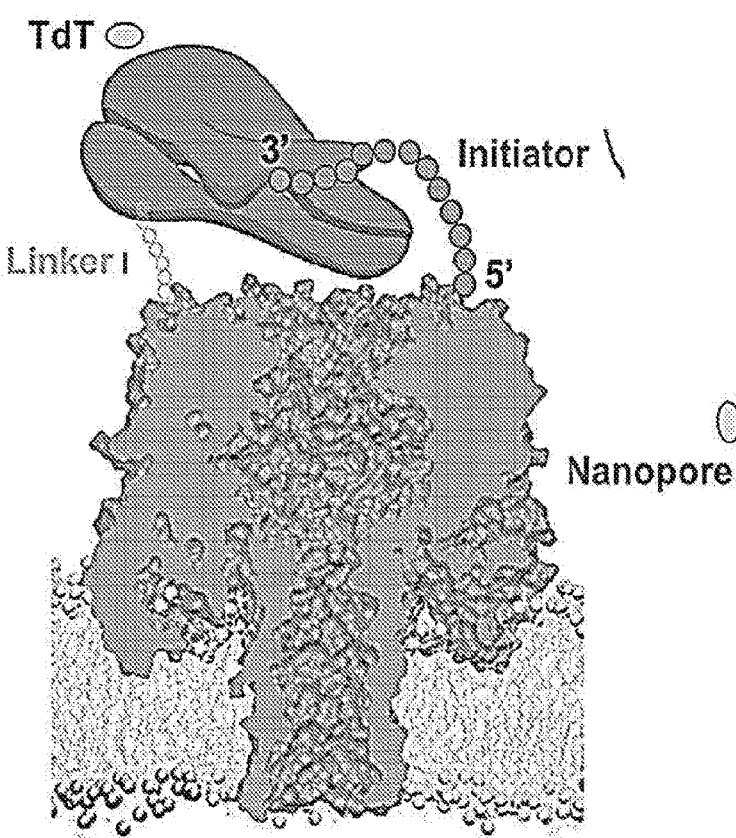
FIGS. 2A-B depict schematics of an encoding unit.
Figure 2B:
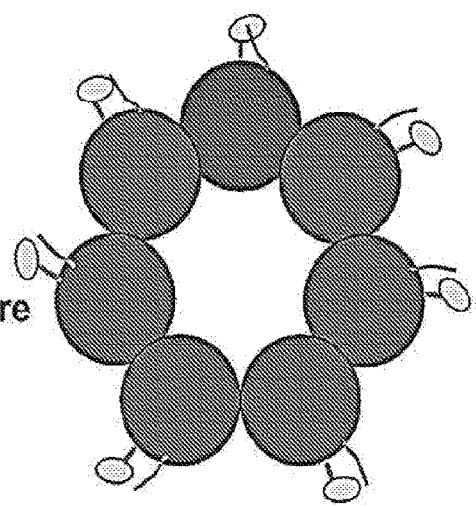

An Encoding Unit:

According to an exemplary embodiment, an encoding unit is formed by tethering one or a plurality of TdT to a protein nanopore such as αHL or MspA as well as 5' immobilizing single-stranded DNA (ssDNA) around the pore rim for initiating synthesis (FIG. 2A). In one embodiment, the tethering is via the SpyCatcher/SpyTag conjugation method. Or alternatively, only the ssDNA is immobilized as described above, while the TdT is in solution for stochastic access to the initiator strand driven by Brownian motion.

Figure 3A:
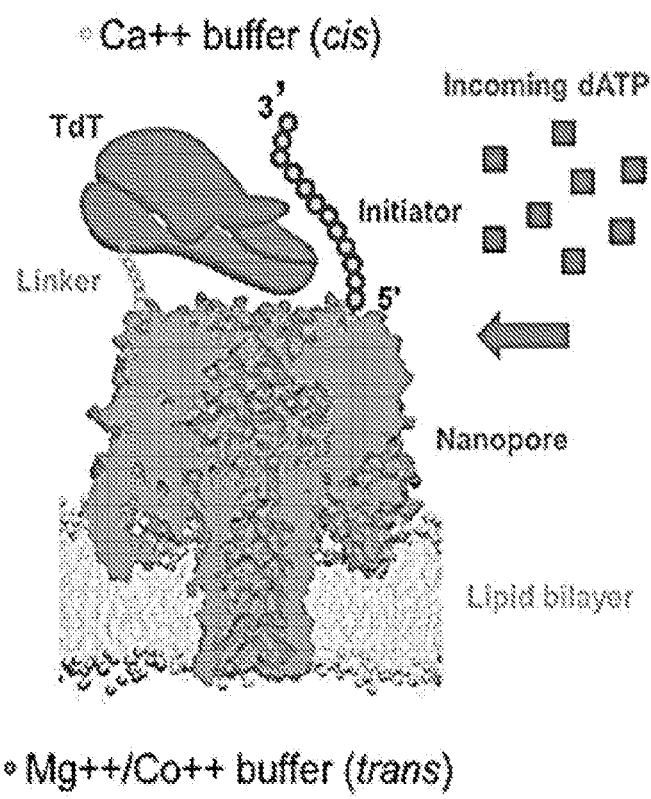
FIGS. 3A-D depict a TdT-based gene synthesis scheme by ion-flux modulation though a nanopore array.

According to an exemplary embodiment, two liquid reservoirs (cis/trans) that are separated by a lipid bilayer are formed on the opposite sides of the lipid bilayer. In one embodiment, the cis side contains non-catalytic buffer ($Ca^{2+}$), which will prevent covalent bond catalysis, i.e., base addition to the 3' end of the primer sequence. In one embodiment, the trans side contains high concentration of catalytic buffer ($Mg^{2+}/Co^{2+}$), which promotes covalent bond catalysis, i.e., base addition to the 3' end of the primer sequence. In one embodiment, an encoding unit is inserted into the lipid bilayer over an electrode, which can modulate voltage across the membrane in a self-addressable manner.
Encoding Algorithm Steps:

According to an exemplary embodiment, in step 1, flowing in dATP (or other nucleotide, one at a time) in non-catalytic buffer ($Ca^{2+}$ or other non-$Mg^{2+}/Co^{2+}$ allowing binding but not covalent bond catalysis), referred to as step 1, "NUCLEOTIDE FLOW" (FIG. 3A).

Figure 3B:
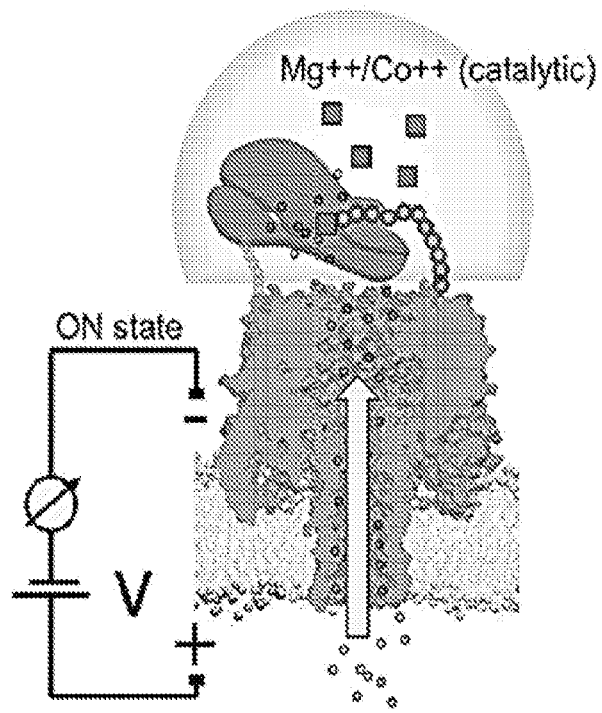

In step 2a, turning the voltage gradient on across membrane (ON state), such that a plume of catalytic ions (Mg++/Co++) is injected to the cis side (from the trans side). The polarity must be cis side negative polarity, trans side positive polarity to force the positively charged ions to migrate to the cis compartment upon activation, referred to as step 2a, "ENZYME ACTIVATION" (FIG. 3B).

A highly localized, hemispheric ion gradient will be generated at this instance immediately outside of the nanopore (αHL), which may be finely controlled via the voltage magnitude and pulse duration. This control is demonstrated theoretically with COMSOL simulations (Anderson, B. N. et al. Probing Solid-State Nanopores with Light for the Detection of Unlabeled Analytes. ACS Nano 8, 11836-11845 (2014)) (FIGS. 4A-C), as well as experimentally using $Ca^{2+}$ sensitive fluorescent activation (Ivankin, A. et al. Label-Free Optical Detection of Biomolecular Translocation through Nanopore Arrays. ACS Nano 8, 10774-10781 (2014)) (FIG. 5). Essentially, it is desirable to generate a locally-saturated reaction volume around the TdT enzyme to promote its catalytic activity, i.e., addition of a single base or a homopolymer run to the ssDNA.

The enzymatic activity of the TdT in the immediate vicinity of each pore is proportional to the catalytic divalent $Mn^{2+}/Co^{2+}$ ion flux through the pore and remains constant as long as the steady flow of ions is maintained. The catalytic ion distribution around the nanopore can be modulated/regulated and thus the enzymatic activity is voltage-tunable.

Figure 3C:
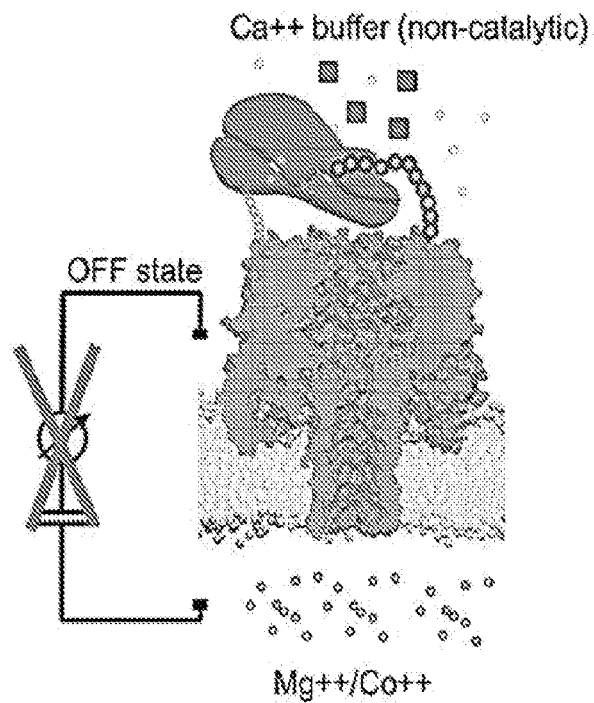

In step 2b, if the voltage gradient is not applied (OFF state), catalytic ion migration will not occur, which will lead to no addition—only transient binding—of a single base to ssDNA, referred to as step 2b, "EZNYME PASSIVATION" (FIG. 3C).

Figure 3D:
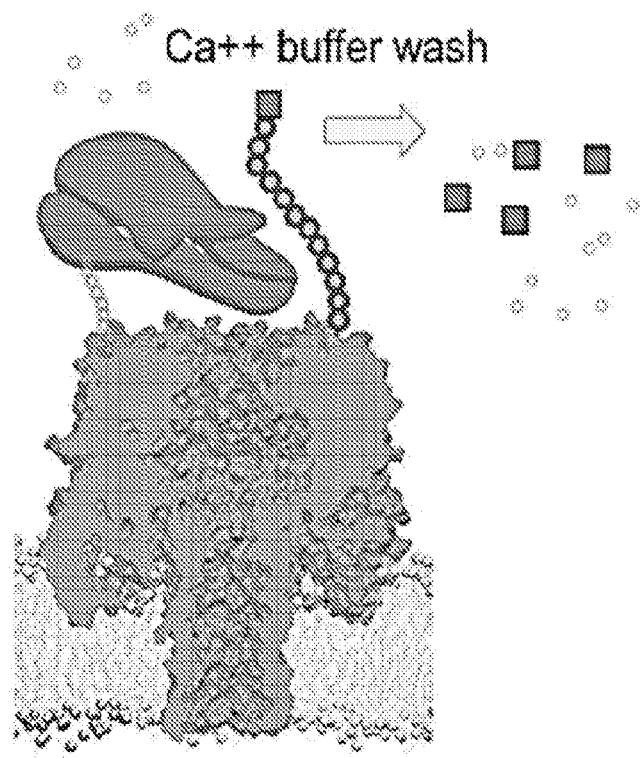
Figure 4A:
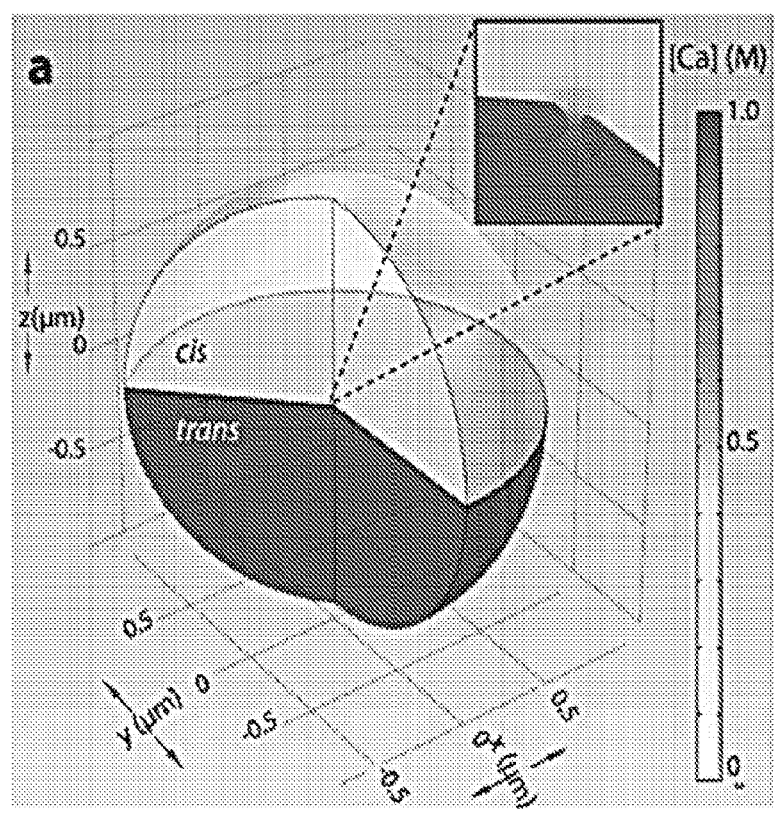
FIGS. 4A-C depict numerical simulations of the steady-state ions spatial distribution near the nanopore.
Figure 4B:
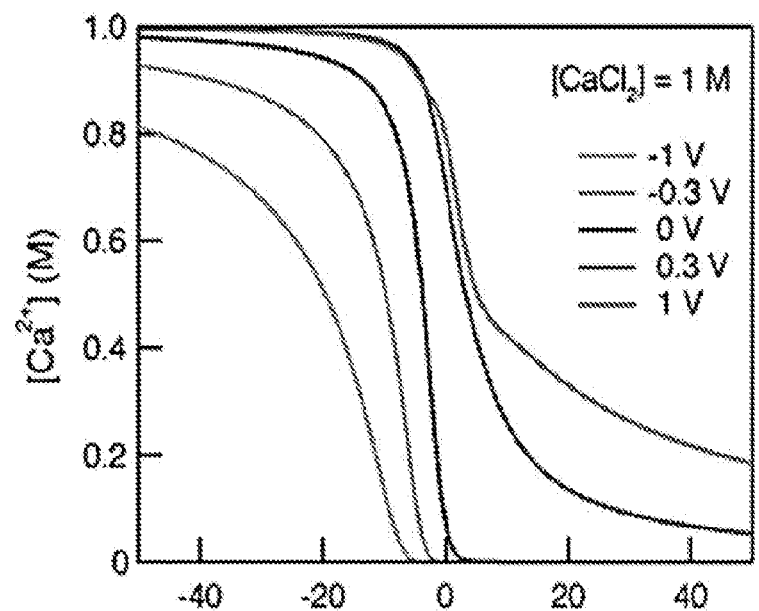
Figure 4C:
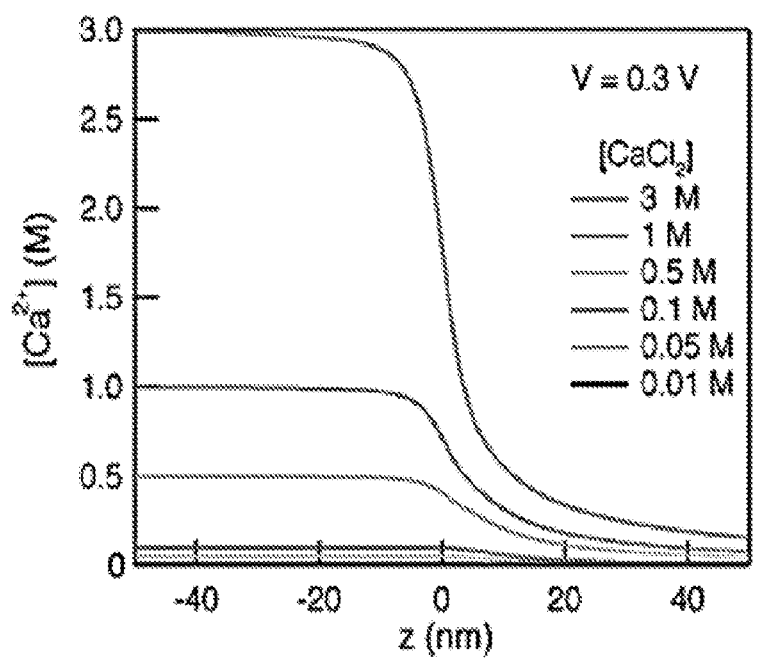
Figure 5A:
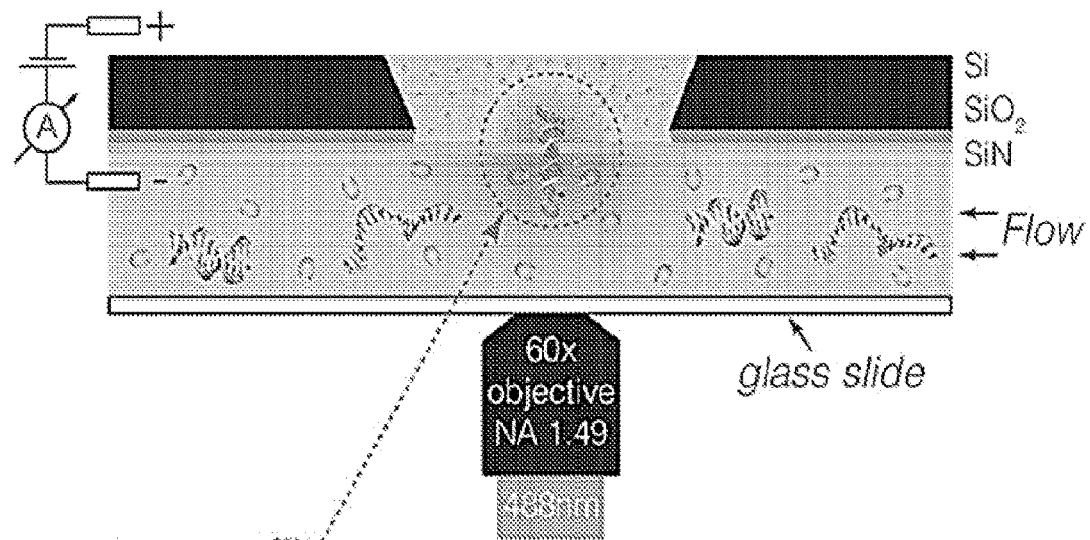
FIGS. 5A-D depict simultaneous electrical and optical readout of ionic current in nanopores.
Figure 5B:
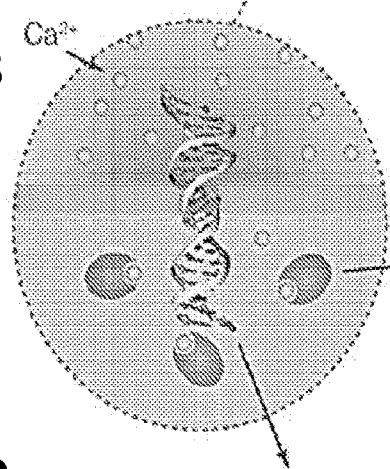
Figure 5C:
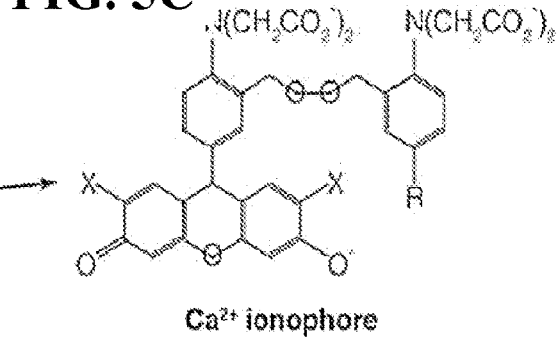
Figure 5D:

In step 3, flushing the cis compartment with fresh non-catalytic buffer to remove any nucleotides and catalytic ion residues, referred to as step 3, "FLUSHING" (FIG. 3D). Note, that the flow rate of this "FLUSHING" step must be optimized such that it does not destroy the lipid bilayer.

Steps 1-3 constitute the gene synthesis cycle for a particular nucleotide. This cycle is repeated with subsequent dTTP, dGTP and dCTP for "NUCLEOTIDE FLOW" iterations with either steps 2a for TdT activation (base or homopolymer addition) or 2b for TdT passivation (no base addition).

More specifically, since the electrodes are self-addressable, at each "NUCLEOTIDE FLOW" step the ON/OFF state can be controlled, i.e., the particular (single or multiple) base incorporation per encoding cycle. In an exemplary embodiment, DNA can be synthesized in a controlled manner (with either at single-base resolution, if there is a very good pulse control; or with homopolymer-resolution, which can be regarded as a distinct states of {A, C, T, G}).
Encoding Schemes:

According to an exemplary embodiment, this scheme can be used to encode information via the base case: 12 possible 2-base state transitions (see below) using standard techniques (Goldman, N. et al. Towards practical, high-capacity, low-maintenance information storage in synthesized DNA. Nature 494, 77-80 (2013)), while read out can be implemented by subsequent DNA sequencing (Illumina or nanopore-based) methods. Depending on the alphabet size to be encoded the state-transition map can be extended with multiple-base transitions (for example a 3-base state transition: A→C→T to accommodate more characters. Every hierarchical dimension can be extended with 3 other states, so it has a multiplicity of 3. Specifically, a 2-state transition map has 12 states, a 3-state transition map has 3*12=36, while an N-state transition map has N*12 unique states.

01. A→C
02. A→T
03. A→G
04. C→A
05. C→T
06. C→G
07. T→A
08. T→C
09. T→G
10. G→C
11. G→T
12. G→A

If single-base synthesis accuracy is achieved via the fine voltage-tunable TdT control, this method can be utilized as a high-throughput gene synthesis.

It was shown that template dependent nanopore-coupled polymerase activity may be modulated in the presence of various cations, such as non-catalytic $Ca^{2+}$, which prevents polymerase catalysis, in which case ion current signal corresponding to base-specific binding events can be observed only as in "static capture" (see FIGS. 4A-C & FIGS. 14A-B). With catalytic $Mn^{2+}$, which promotes polymerase catalysis, in which case ion current signal corresponding to template progression can be observed as in "real sequencing" (see FIGS. 5A-D).

It has been demonstrated that each case has the expected enzymatic effects when in saturated concentration regimes (3 mM $Ca^{2+}$, 0.1 mM $Mn^{2+}$).

Using the already established nanopore-array platform, specific nucleotides or homopolymer runs can be encoded into self-priming DNA hairpins in a template-dependent manner. Voltage functions can be established to appropriately control the ion-flux through the nanopore, where optimal voltage magnitude and pulse duration parameters can be established. After establishing these fine-tuning parameters, TdT enzymes instead of φ29 polymerase can be coupled to the nanopore as shown in FIG. 2. Alternatively, the synthesis efficiency and accuracy can be evaluated using TdT in solution—without tethering it/them to the pore. Enzymatic activity can also be monitored via continuous imaging of incorporating fluorescently labeled nucleotides inhibited or promoted by the non-catalytic ($Ca^{2+}$) or catalytic ($Mn^{2+}/Co^{2+}$) ion gradient, while running the already established voltage modulation protocols for activation/deactivation. Processivity of TdT may be boosted with the fusion of single-strand binding proteins (SSB), such as TdiF.
High-throughput Scaling:

According to an exemplary embodiment, an electrode area is a circle with diameter, $D_e$=5 μm, the electrode surface area is, $A_e$=20 μm². In one embodiment, the αHL pore area is assumed such that the pore outer diameter is $D_p$=80 Å=0.008 μm, the pore surface area is, $A_p$=5×10⁻⁵ μm².

Figure 6:
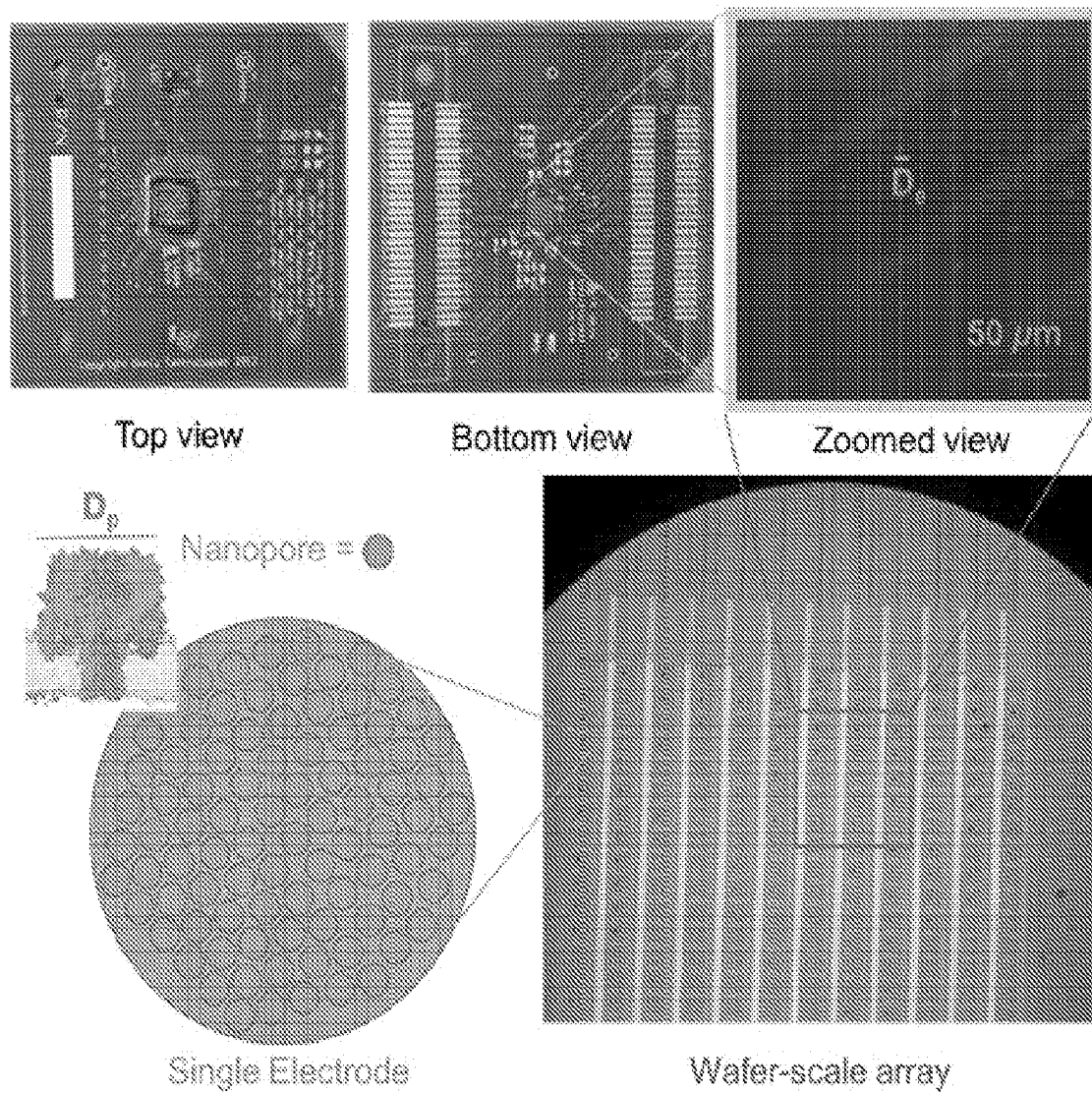
FIG. 6 shows various views of a demonstration of maximum packing density of a single electrode array surface area with αHL nanopores. Not to scale.
Figure 7:
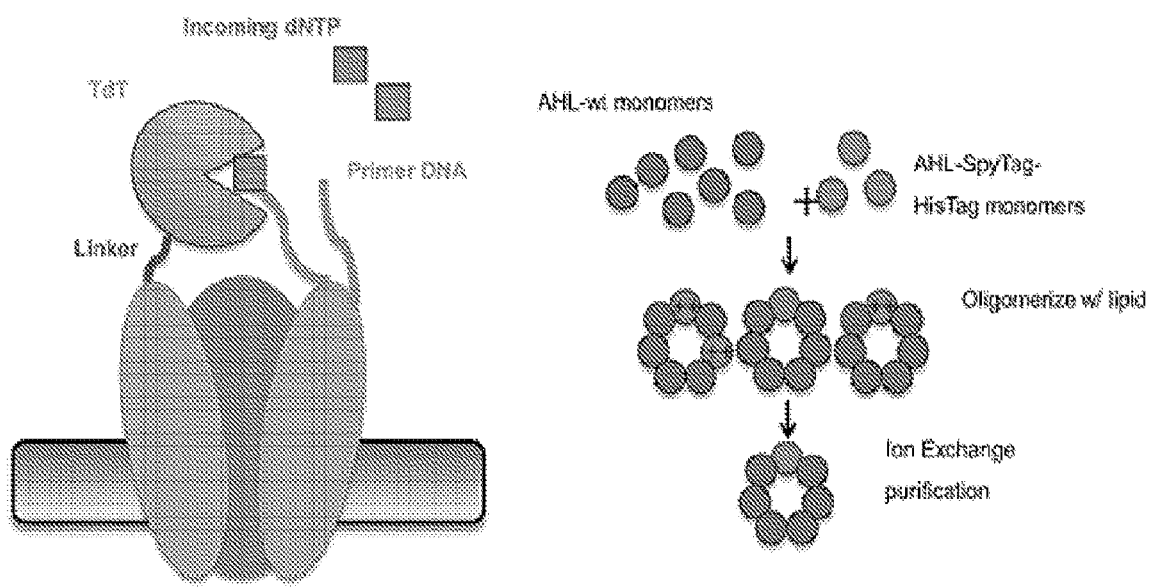
FIG. 7 depicts schematics of information encoding and/or decoding of the nanopore-based system.
Figure 8:
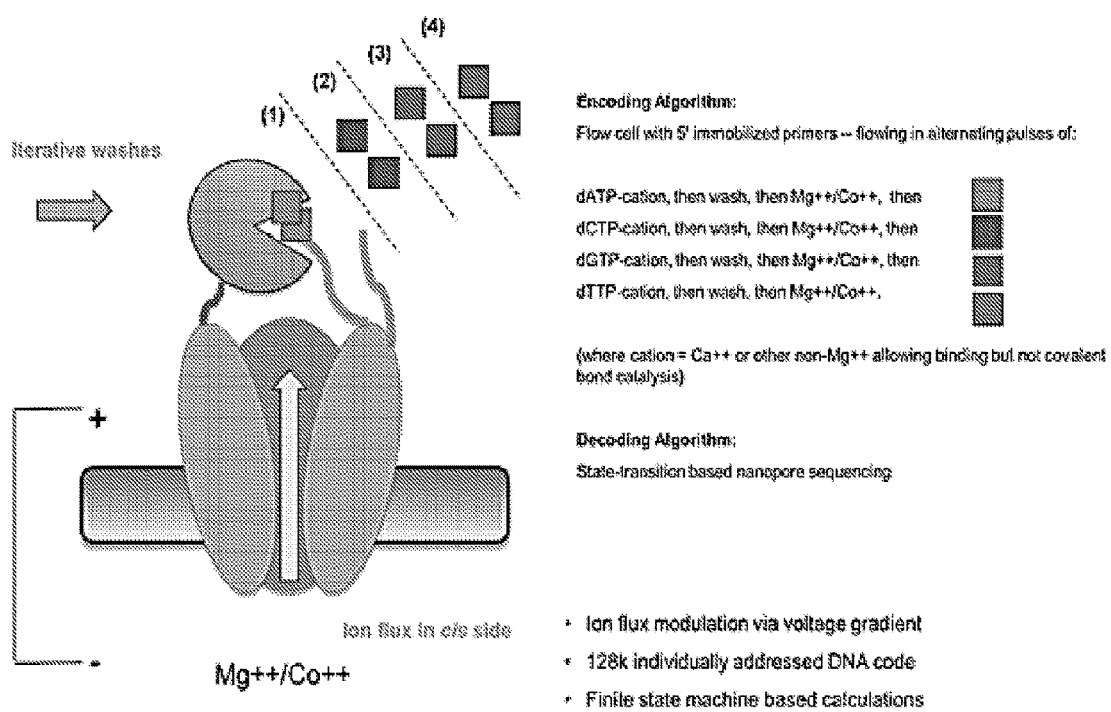
FIG. 8 depicts schematics of information encoding and/or decoding of the nanopore-based system.

In one embodiment, about 400,000 pores can be fitted above an electrode with maximum packing density, but it can be assumed that in reality there will be a 10% insertion rate. This translates to about 40,000 pores per electrode (FIG. 6). Each pore can accommodate seven TdT molecules in theory (FIG. 2B), so each can synthesize a strand with the similar information (A,C,T,G) content based on ion-flux modulation. So, each electrode area can accommodate about 40,000 encoding units of the same type (like a local "amplification" or encoding cluster).

In one embodiment, for a 128,000 electrode-containing chip, it may synthesize 128,000 different species of DNA (=gene or a string of information with a 40,000-fold amplification—can help with minimizing error).

Example II

Information Encoding with a DNA Polymerase-coupled Nanopore

Figure 9:
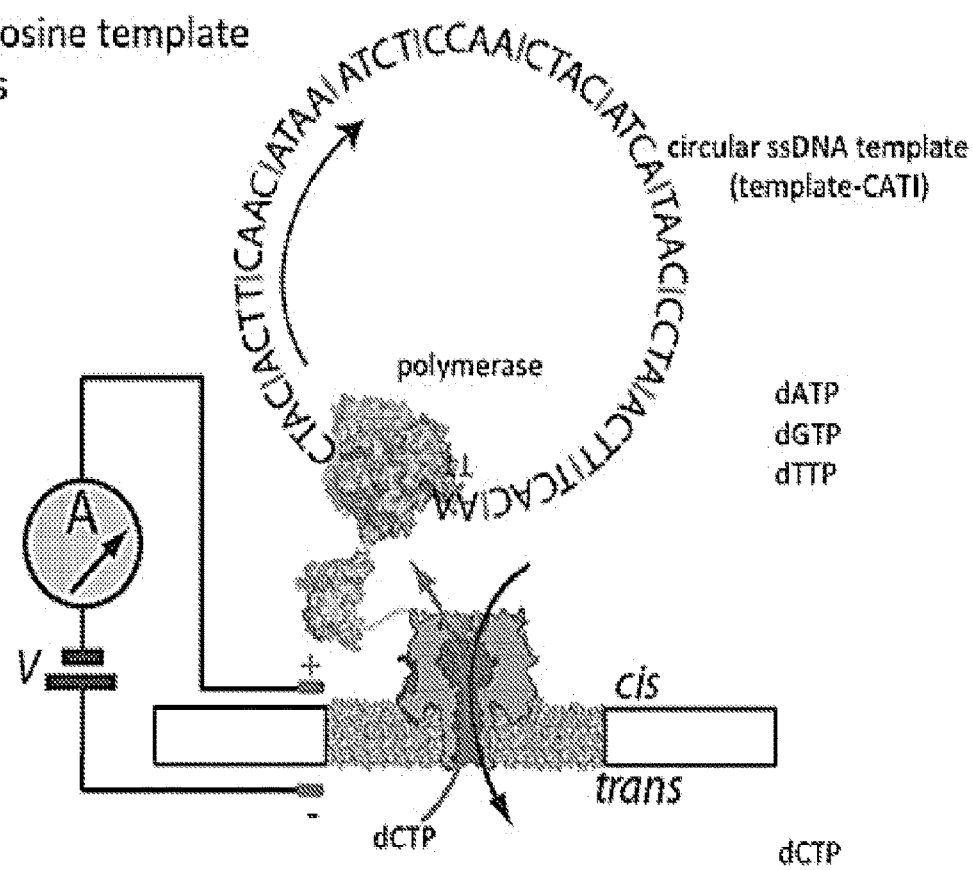
FIG. 9 depicts a schematic of circular inosine template with no Gs (SEQ ID NO: 3). dCTP (only present in the trans solution) flows through the pore and is incorporated into the complement strand during polymerization only if the polarity of the applied voltage (cis positive) forces it through the pore into the proximity of the polymerase.
Figure 10:
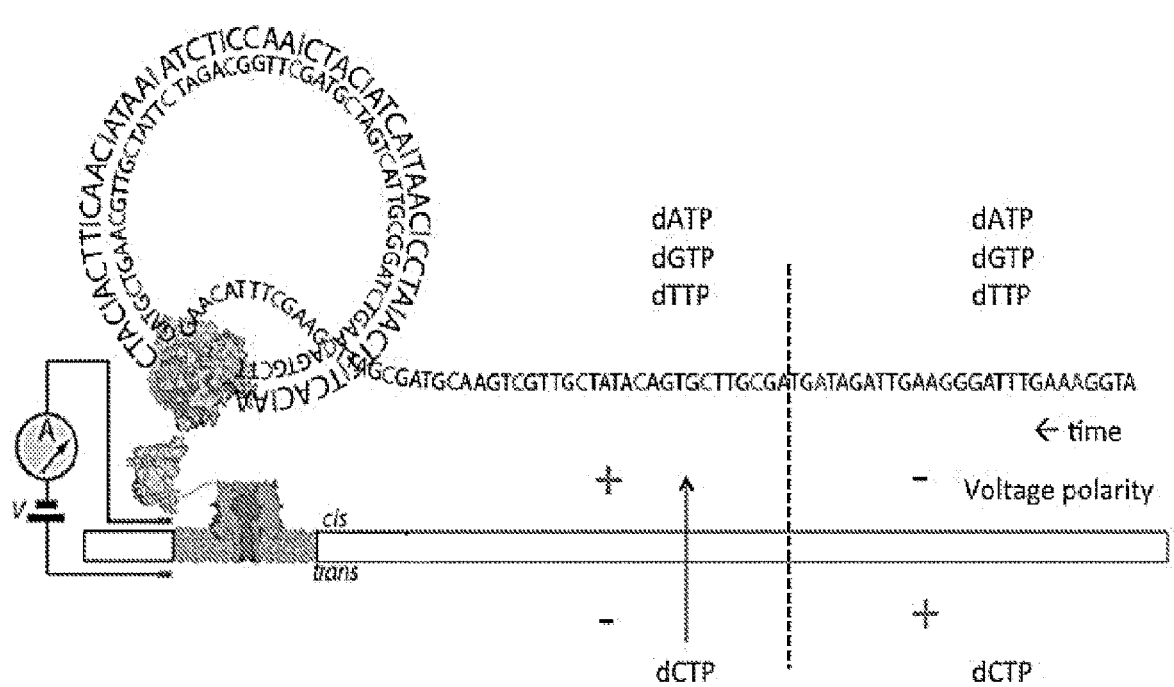
FIG. 10 depicts a schematic of a voltage recorder embodiment of the nanopore-based system.

DNA polymerases (e.g. phi-29 DNAP) preferentially incorporate dCTP when copying a template containing inosine bases. In the absence of dCTP, the polymerase will incorporate dATP, dGTP, or dTTP (in order of decreasing preference). This example describes an information encoding system comprising a DNA polymerase (e.g. phi 29 DNAP)-coupled nanopore (alpha hemolysin) and a circular ssDNA template strand containing some sequence of cytosine, adenine, thymine, and inosine bases (template-CATI) (FIG. 9). The polymerase and ssDNA template is tethered on the cis side of the nanopore. Also present in the cis solution are dATP, dGTP, and dTTP (in addition to other cofactors and salts required for polymerase activity). In the trans solution, only dCTP is present (in addition to the other cofactors and salts). The information encoding method described herein employs standard DNA sequencing conditions, the co-factors and salts are well-established in the art and are known to a skilled in the art. When a voltage is applied across the nanopore (cis side positive), the negatively charged dCTP molecules are electrophoretically forced through the pore and into the proximity of the polymerase-template complex. If the polymerase is actively copying the template-CATI strand to produce the complement strand during this time, cytosine is preferentially incorporated into the nascent complement strand during synthesis at sites that complement the inosine of the template strand. However, when the polarity of the voltage is reversed (i.e. cis side negative), dCTP no longer flows through the pore, and the polymerase is no longer able to incorporate cytosine into the complement strand. That is, dATP, dGTP, or dTTP must be incorporated instead. Thus, this system "records" the voltage polarity applied across the nanopore over time by encoding this information into a complement strand of DNA during polymerization of the template strand. Information is stored in the complement strand in the form of regions of bases either containing or lacking cytosine bases at the sites which complement the inosine bases of the template strand, and this translates to the "1" or "0" state of a single bit of information (FIG. 10).

Example III

Single Molecule Attachment Strategy for High-Throughput Nanopore Measurement

Figure 11:
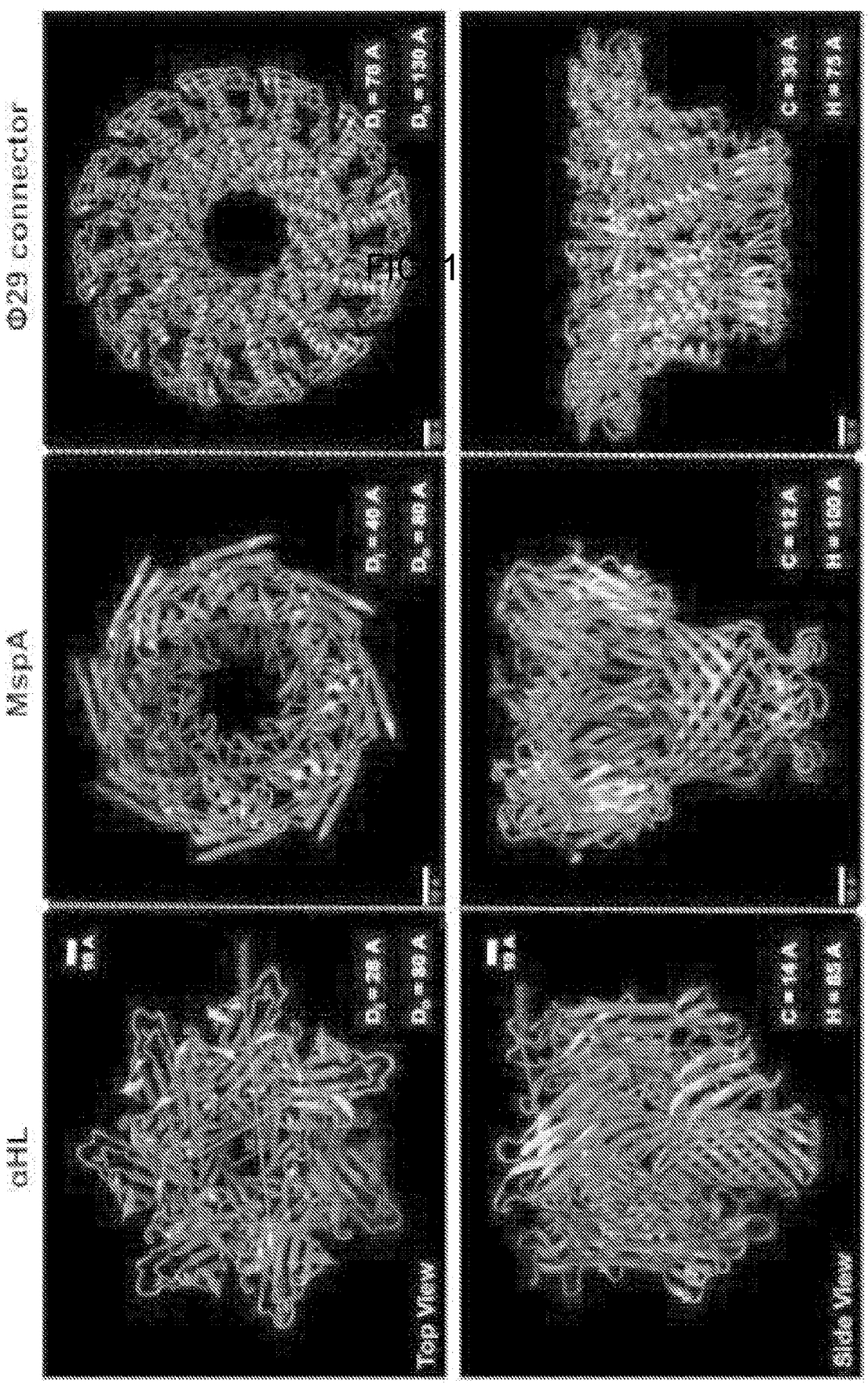
FIG. 11 shows that various types of membrane channels can be used to tether a single enzyme with the proposed strategy for single molecule ion current measurement.

This example describes a novel design and experimental characterization of an attachment strategy to precisely couple a φ29 polymerase molecule (or potentially any other enzyme) to a αHL nanopore (or potentially any other type of membrane channel, such as MspA, φ29 connector, etc.—see FIG. 11) for single molecule (SM) measurement (FIGS. 12A-D). In this work, a specific application of this strategy—namely DNA sequencing—was demonstrated by observing the SM incorporation events associated with the catalytic step of the polymerase during complementary (FIGS. 13A-D and FIGS. 14A-B) and successive (FIGS. 15A-B) tagged nucleotide incorporation into a template DNA. The method of isolating a 1:6 αHL nanopore, followed by addition of a single covalently bound polymerase could be extended to other methods of single molecule detection via a nanopore. Single molecule enzyme activity, or protein-protein interactions could be observed by coupling the desired molecular event to the alteration of current through the pore. This technology could serve as the basis for the design of a host of new, high-throughput molecular sensors.

One attachment pair or moiety for the attachment of the polymerase to the pore is SpyTag/SpyCatcher. The method is described in U.S. patent application Ser. No. 13/578,070, published as US20130053544. The method is not specific to nanopore/polymerase/sequencing. Another general strategy of nucleic acid sequencing is described in U.S. patent application Ser. No. 14/073,445, published as US20140134616.

Figure 12A:
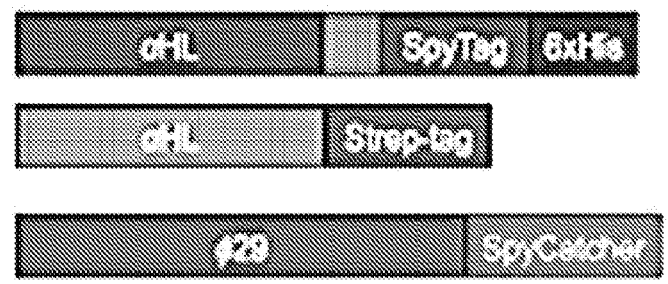
FIGS. 12A-D depict the assembly of the porin-polymerase construct.
Figure 12B:
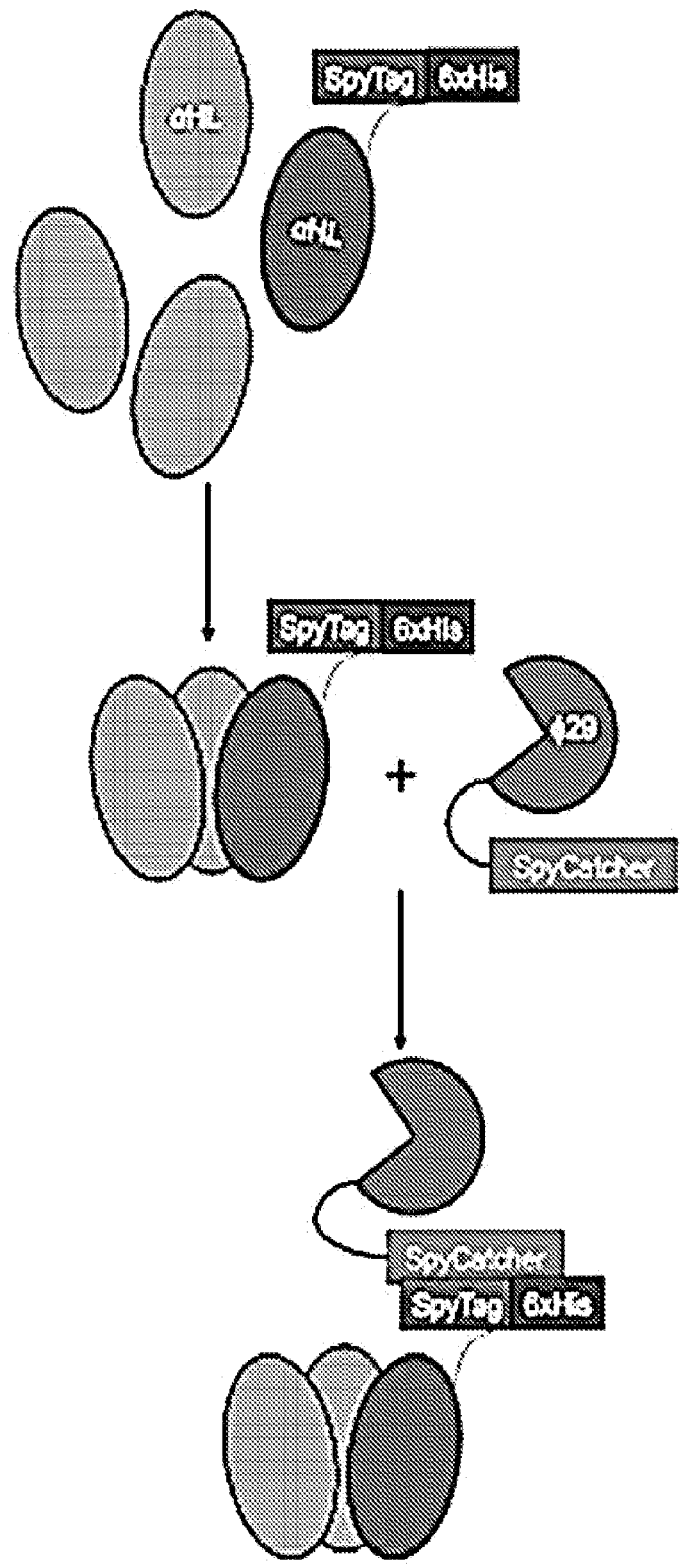
Figure 12C:
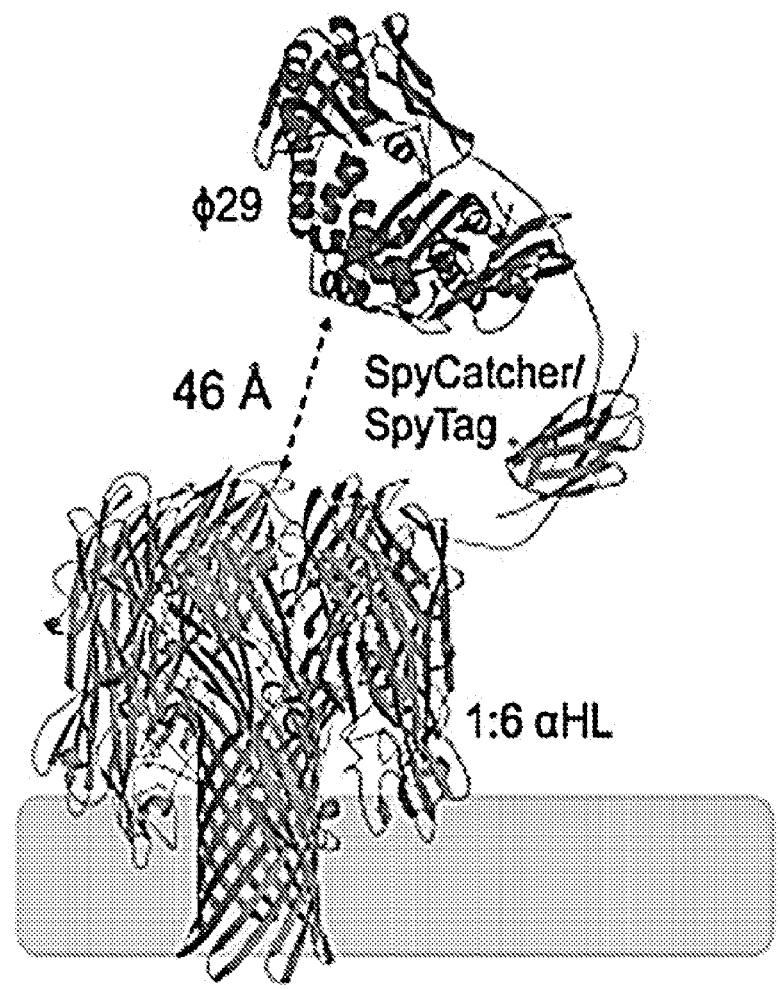
Figure 12D:
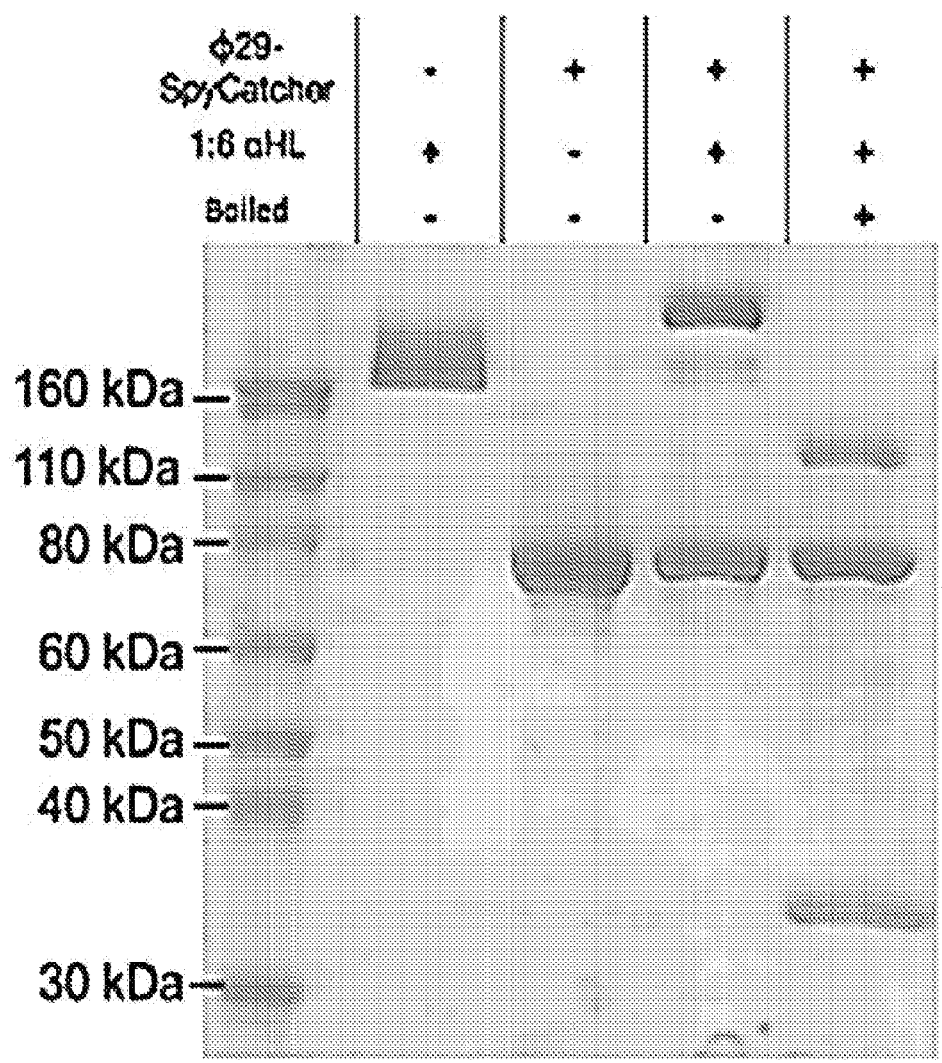
Figure 13A:
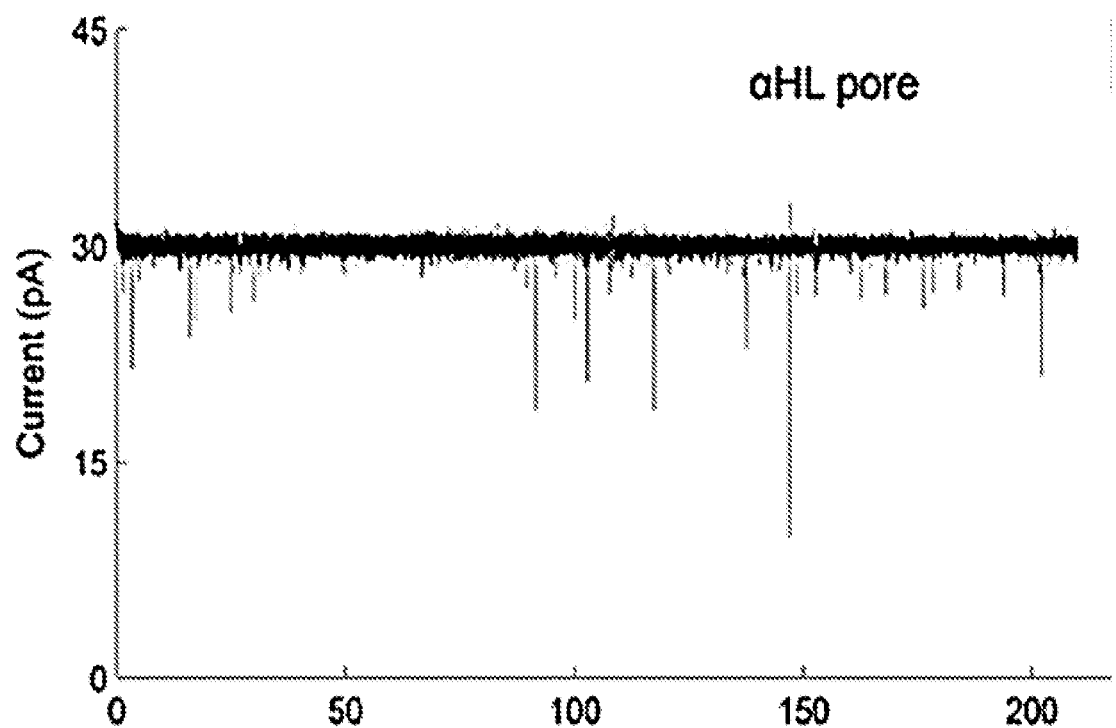
FIGS. 13A-D show representative current versus time traces for the various stages of the pore assembly. When neither tagged nucleotide nor polymerase is present, only stable open channel current is observable.
Figure 13B:
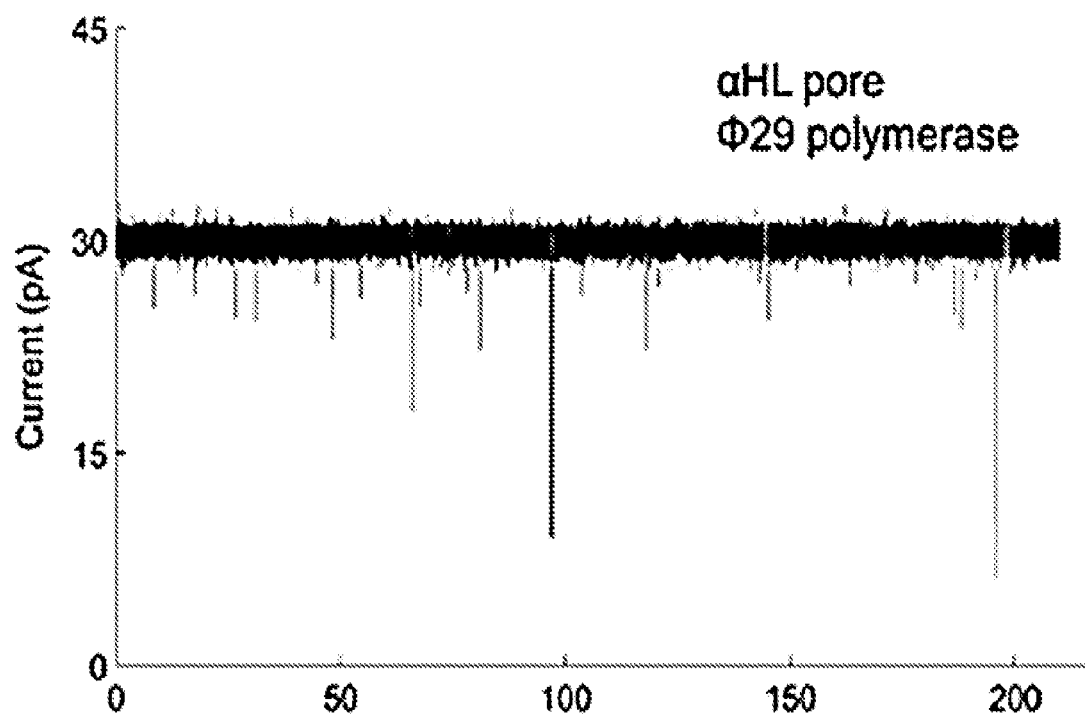
Figure 13C:
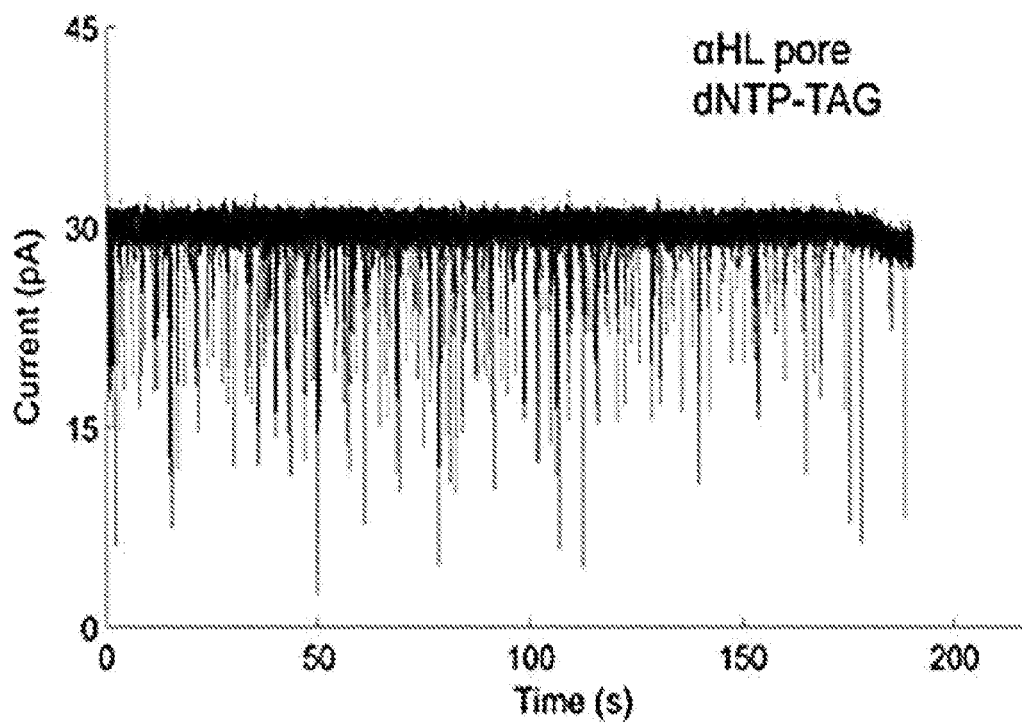
Figure 13D:
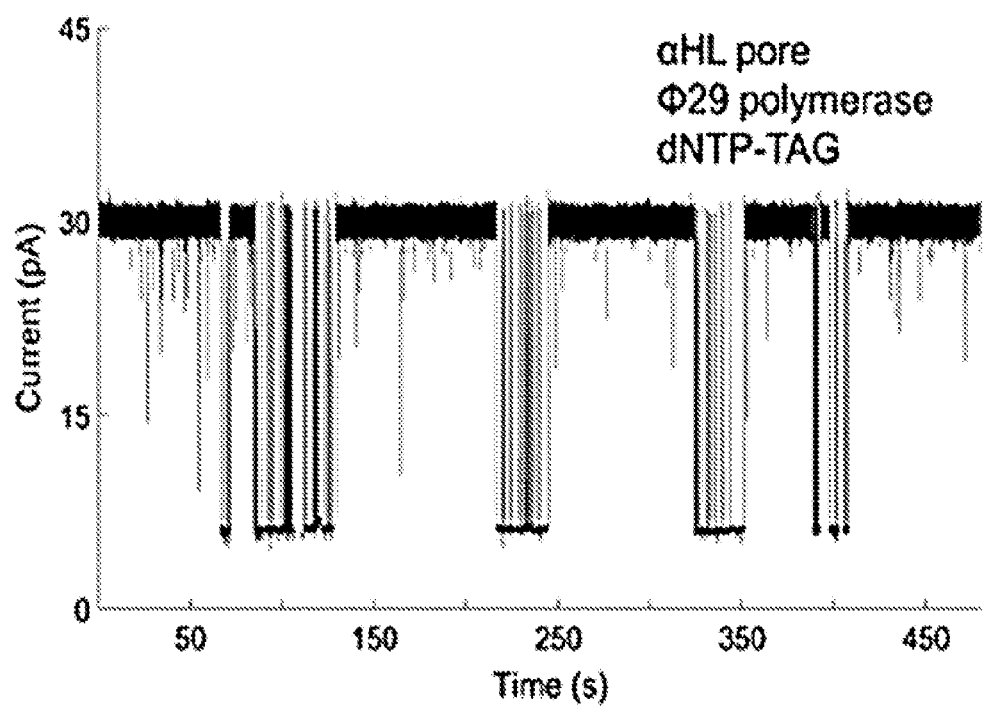

In this example, the SpyCatcher/SpyTag (Zakeri, B.; Fierer, J. O.; Celik, E.; Chittock, E. C.; Schwarz-Linek, U.; Moy, V. T.; Howarth, M. Peptide Tag Forming a Rapid Covalent Bond to a Protein, through Engineering a Bacterial Adhesin. Proc. Natl. Acad. Sci. 2012, 109, E690-E697) protein conjugation system was adopted to couple a single polymerase with one αHL heptamer. Previous work had demonstrated that it was possible to purify a 1:6 heptameric pore, where one subunit contains a C-terminal 6×-histidine tag (6×-His-tag) (SEQ ID NO: 1) and the other six contain neutral Strep-tags (Davis, R.; Chen, R.; Bibillo, A.; Korenblum, D.; Dorwart, M. Nucleic Acid Sequencing Using Tags. US20140134616, 2014). An αHL pore coupled to a single polymerase molecule was made from three proteins: αHL with a C-terminal Strep-tag, αHL with a C-terminal SpyTag peptide followed by a 6×-His-tag (SEQ ID NO: 1), and φ29 with a C-terminal SpyCatcher (FIG. 12A). The whole porin-polymerase conjugate was assembled stepwise, by first forming and purifying the 1:6 (SpyTag:unmodified) αHL pore, followed by addition of φ29-SpyCatcher (FIG. 12B). Amino acid linker lengths between αHL-SpyTag and φ29-SpyCatcher were chosen based on assembling the structures of these proteins (Song, L.; Hobaugh, M. R.; Shustak, C.; Cheley, S.; Bayley, H.; Gouaux, J. E. Structure of Staphylococcal Alpha-Hemolysin, a Heptameric Transmembrane Pore. Science 1996, 274, 1859-1866; Berman, A. J.; Kamtekar, S.; Goodman, J. L.; Lázaro, J. M.; de Vega, M.; Blanco, L.; Salas, M.; Steitz, T. a. Structures of phi29 DNA Polymerase Complexed with Substrate: The Mechanism of Translocation in B-Family Polymerases. EMBO J. 2007, 26, 3494-3505) into a porin-polymerase conjugate followed by macromolecular modeling of the linkers using Rosetta (Leaver-Fay, A.; Tyka, M.; Lewis, S. M.; Lange, O. F.; Thompson, J.; Jacak, R.; Kaufman, K.; Renfrew, P. D.; Smith, C. A.; Sheffler, W.; et al. ROSETTA3: An Object-Oriented Software Suite for the Simulation and Design of Macromolecules. Methods Enzymol. 2011, 487, 545-574.) FIG. 12C. Protein sequences are detailed in FIG. 16.

Experimental Methods

Protein Expression and Purification

The φ29 DNA polymerase—SpyCatcher construct with an N-terminal Strep-tag was expressed in BL21 DE3 Star cells by growing them in Magic Media (Invitrogen, Grand Island, N.Y.) at 37° C. until OD~0.6, followed by overnight growth at 25° C. Cells were resuspended and lysed by sonication in Polymerase Buffer (PolBuff): 50 mM Tris pH 7.5, 150 mM NaCl, 0.1 mM EDTA, 0.05% (v/v) Tween-20, 5 mM 2-mercaptoethanol. Benzolase nuclease was added post cell lysis to remove excess bound DNA. The protein was purified using Streptactin columns per manufacturer's instructions (IBA, Goettingen, Germany). Purified protein was eluted with PolBuff with added desthiobiotin. Both αHL-Strep-tag and αHL-SpyTag-6×-His ("6×-His" disclosed as SEQ ID NO: 1) were expressed in BL21 DE3 Star pLys-S cells grown in Magic Media for 8 hours at 37° C. Each was lysed by sonication in 50 mM Tris pH 8.0, 200 mM NaCl. Strep-tagged αHL was purified on Streptactin columns, and eluted in the same buffer with desthiobiotin. His-tagged αHL was purified with a cobalt column and eluted with 300 mM imidazole.

1:6 Porin Assembly Formation and Isolation

To form a 1:6 SpyTag:unmodified αHL pore, purified αHL proteins were mixed in a ratio of 1:9 SpyTag construct: unmodified. The lipid 1,2-diphytanoyl-sn-glycero-3-phosphocholine (DPhPC) was added to a final concentration of 5 mg/mL, followed by incubation at 40° C. for 30 mins. Lipid vesicles were subsequently popped by adding n-octyl-β-D-glucoside (βOG) to 5% (v/v). Fully formed oligomers were separated from vesicles and monomers by size exclusion chromatography (SEC) in 20 mM HEPES pH 7.5, 75 mM KCl and 30 mM βOG. Oligomeric protein obtained from the SEC was then run on a MonoS column in 20 mM MES pH 5.0, 0.1% Tween-20 and eluted with a linear gradient to 2.0 M NaCl. The desired 1:6 assembly eluted after the 0:7 porin since the 1:6 assembly contains a 6×-His-tag (SEQ ID NO: 1). The 1:6 composition was confirmed by adding SpyCatcher protein and observing a size shift of the conjugate on an SDS polyacrylamide gel indicative of only one SpyCatcher molecule per assembled pore.

Polymerase and Template Attachment

Purified φ29 and the desired template were bound to the pore by incubating two molar equivalents of polymerase and four equivalents of DNA template per 1:6 pore overnight at 4° C. The full tertiary complex was isolated by SEC in 20 mM HEPES pH 7.5, 150 mM KCl, 0.01% Tween-20, 5 mM TCEP. Isolated fractions were characterized by SDS PAGE to confirm the presence of φ29 and αHL conjugate. Formed complexes were tested for polymerase function by rolling circle amplification.

Lipid Bilayer Formation

Synthetic lipid 1,2-di-O-phytanyl-sn-glycero-3-phosphocholine (Avanti Polar Lipids, Alabaster, Ala.) was diluted in tridecane (Sigma-Aldrich, St. Louis, Mo.) to a final concentration of 15 mg/mL. A single lipid bilayer was formed on a silanized CMOS chip surface containing an array of 264 Ag/AgCl electrodes. The automated lipid spreading protocol utilized an iterative buffer and air bubble flow to mechanically thin the membrane. During this step, current was applied across the lipid bilayer in order to detect its capacitance, which directly correlates to structural integrity of the membrane. An empirically determined capacitance threshold value of 5 fF/µm$^2$ was used to classify the properly formed, single lipid bilayer to conclude the thinning protocols.

Pore Insertion

The automated pore insertion method consisted of two voltage protocols: (1) initially constant DC voltage was applied at 160 mV for 1 min, immediately followed by (2) a linearly increasing voltage ramp from 50 mV to 600 mV with a 1 mV/s incremental step. The smoothly increasing voltage gradient amplified the electrical driving force guiding the nanopores into the lipid bilayer. If a cell became active, i.e., started to record current in the pA regime, we considered this event a pore insertion, due to the measured increase in conductance across the bilayer. Immediately after this event, this cell was turned off to prevent additional pore insertions. In this way, the probability of multiple pore insertions above the same electrode array element was minimized.

Nanopore Experiments

All ternary complex capture (TCC) experiments were performed in a buffer containing 300 mM NaCl, 3 mM $CaCl_2$—providing the non-catalytic divalent cations to probe nucleotide binding/unbinding events—and 20 mM HEPES pH 7.5. For sequencing experiments, this buffer was modified by replacing $CaCl_2$ with 0.1 mM $MnCl_2$ as a catalytic cation source during the polymerase extension reaction to initiate and sustain sequential nucleotide additions along the template DNA. Purified porin-polymerase-template conjugates were diluted in buffer to a final concentration of 2 nM. After pumping a 5 µL aliquot to the cis compartment, single pores were embedded in the planar lipid bilayer that separates two compartments (denoted cis and trans) each containing ~3 µL of buffer solution. Experiments were conducted at 27° C. with 5 µM tagged nucleotides added to the cis well.

Data Acquisition

The ionic current though the nanopore was measured between individually addressable Ag/AgCl electrodes coupled to a silicon substrate integrated electrical circuit. This consisted of an integrating patch clamp amplifier (Genia Technologies, Mountain View Calif.), which provided a constant 100 mV potential across the lipid bilayer in voltage clamp mode. Data were recorded at a 1 kHz bandwidth in an asynchronous configuration at each cell using circuit-based analog-to-digital conversion and noise filtering (Genia Technologies, Mountain View Calif.), which allows independent sequence reads at each pore complex. During the various experimental steps, a precision syringe pump (Tecan, Männedorf, Switzerland) was utilized in an automated fashion to deliver reagents into the microfluidic chamber of the CMOS chip at a flow rate of 1 µL/s. Software control was implemented in Python, which interfaced with the pump via an RS 232 communication protocol.

Event Detection and Data Analysis

Ionic current blockade events were identified using a custom event detection algorithm implemented in MATLAB (2014b, MathWorks, Natick, Mass.). Briefly, an event was identified by selecting segments that deflected from open channel current ($I_O$=~30 pA at 100 mV in 300 mM NaCl, 3 mM $CaCl_2$ and 20 mM HEPES pH 7.5) below a cutoff value of 70% of $I_O$ (21 pA) to a stable current level ($I_B$) with a minimum dwell time of >10 ms. For each nanopore experiment, event searches were performed to obtain the average residual current level (with respect to open channel) for each capture event ($I_{RES}$). Statistical analysis was performed to determine the mean, median and standard deviation of each capture event by fitting a Gaussian to a histogram of $I_B$ values. The residual current blockade was defined as: $I_{RES}$ %=$I_{RES}/I_O$, while the duration of the event in the deflected segment corresponds to the dwell time. Mean dwell time and residual current of each event in an experimental set was accumulatively quantified using scatter plots and box-and-whisker plots. On each box plot, the central red mark represents the median, while the bottom and top blue edges of the box are the $1^{st}$ and $3^{rd}$ quartile median values respectively. The whiskers extend to the lowest and highest values within 1.5 IQR of the $1^{st}$ and $3^{rd}$ quartile medians. Alternatively, average dwell time/residual current probability histograms were generated by plotting each bin normalized by the total number of observed events.

Classification of Capture Events

Figure 14A:
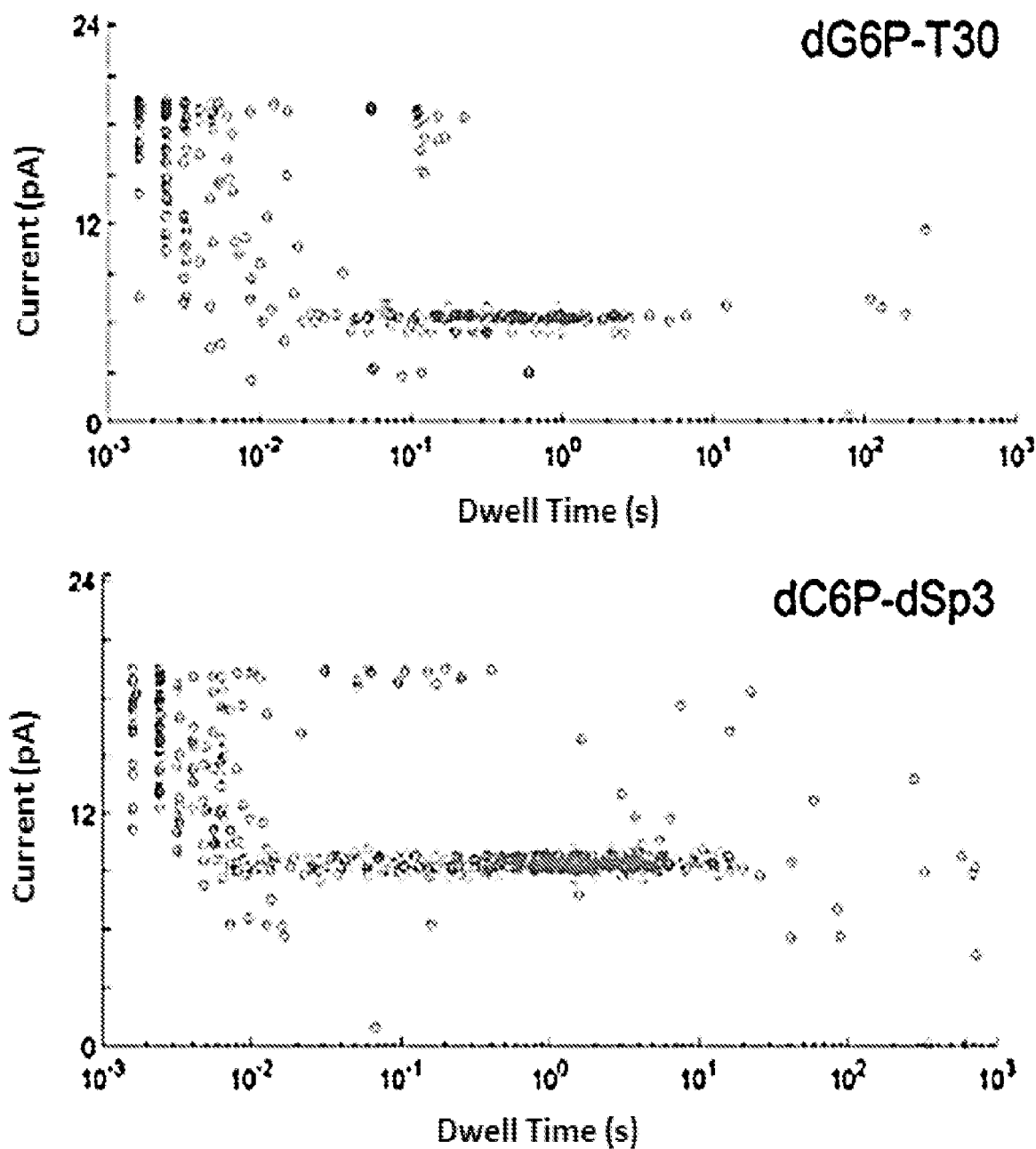
FIGS. 14A-B show base discrimination of the four tagged nucleotides on a semi-conductor chip array. All measurements were taken on a pore-polymerase-template complex under non-catalytic conditions where the first base on the template is complementary to the added tagged nucleotide.
Figure 14A:
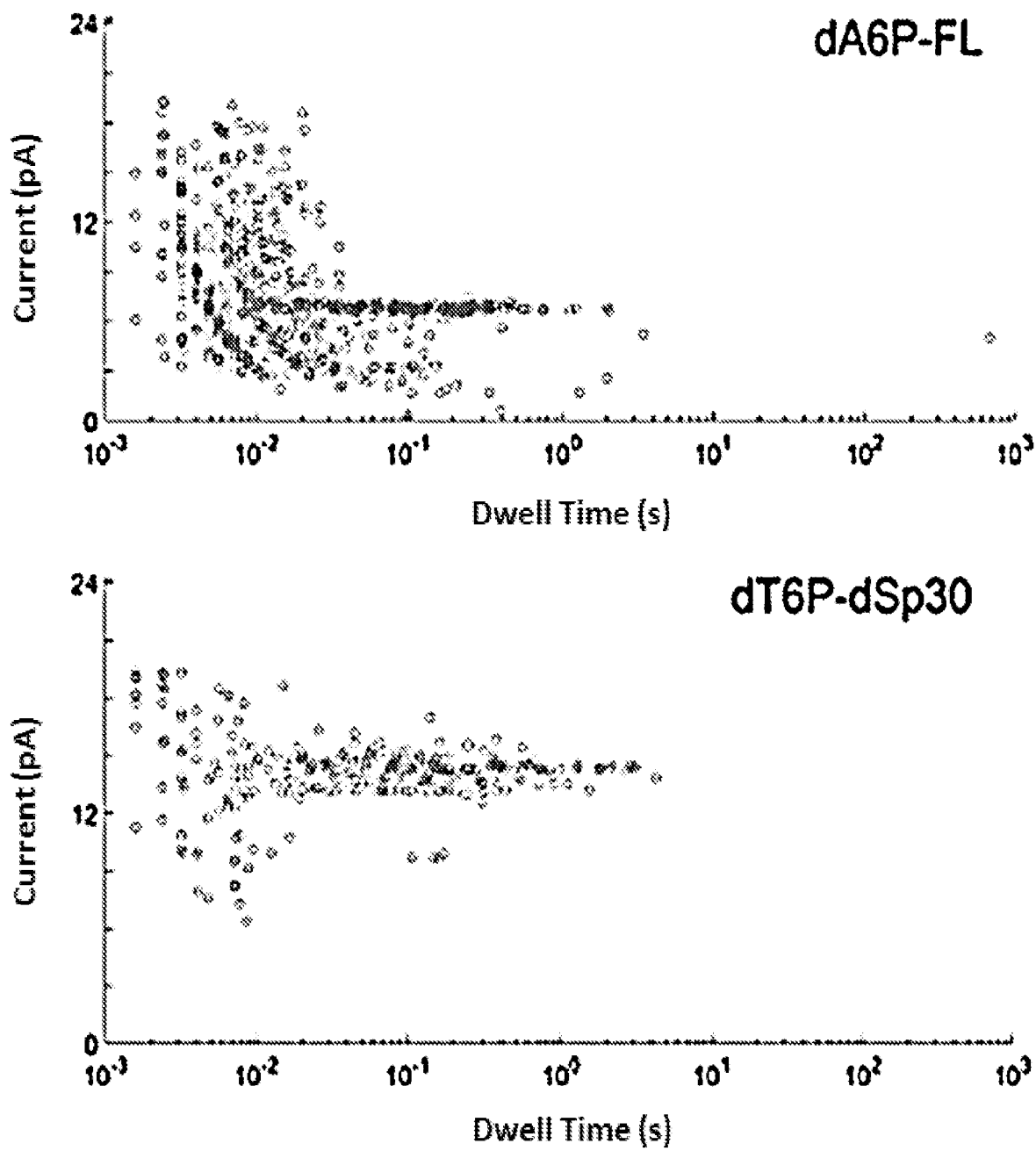
Figure 14B:
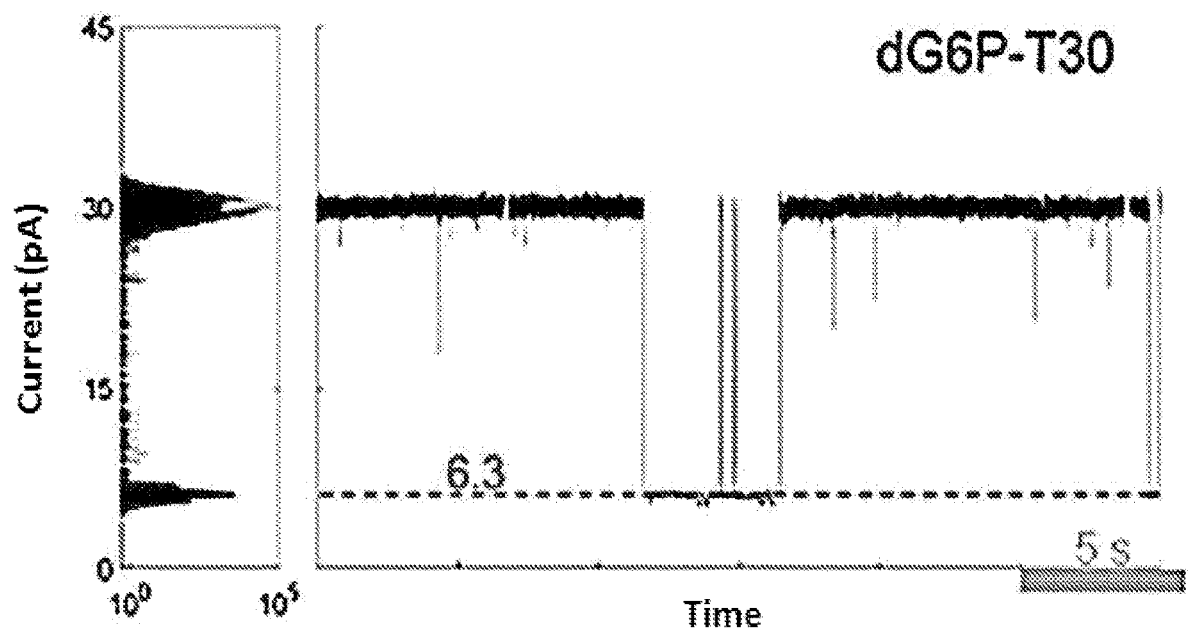
Figure 14B:
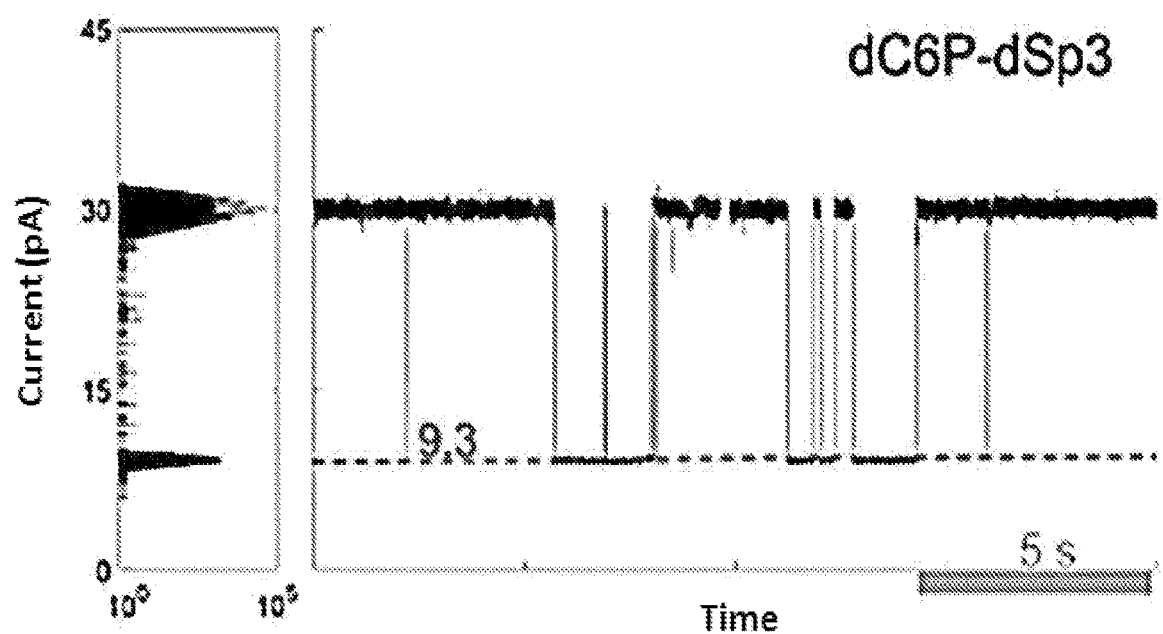
Figure 14B:
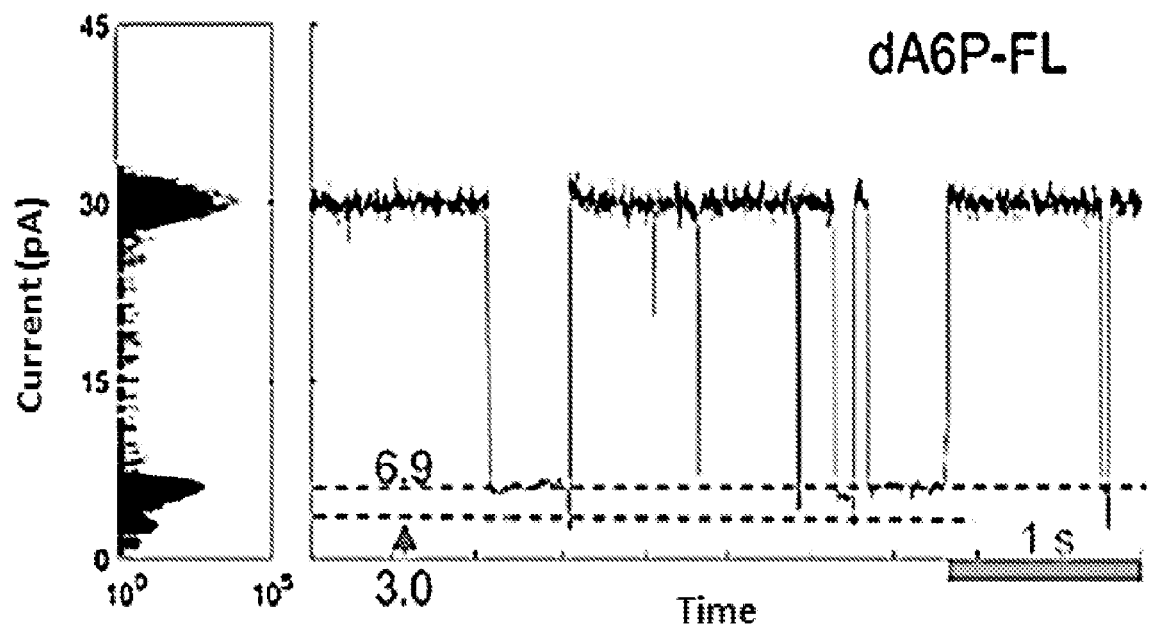
Figure 14B:
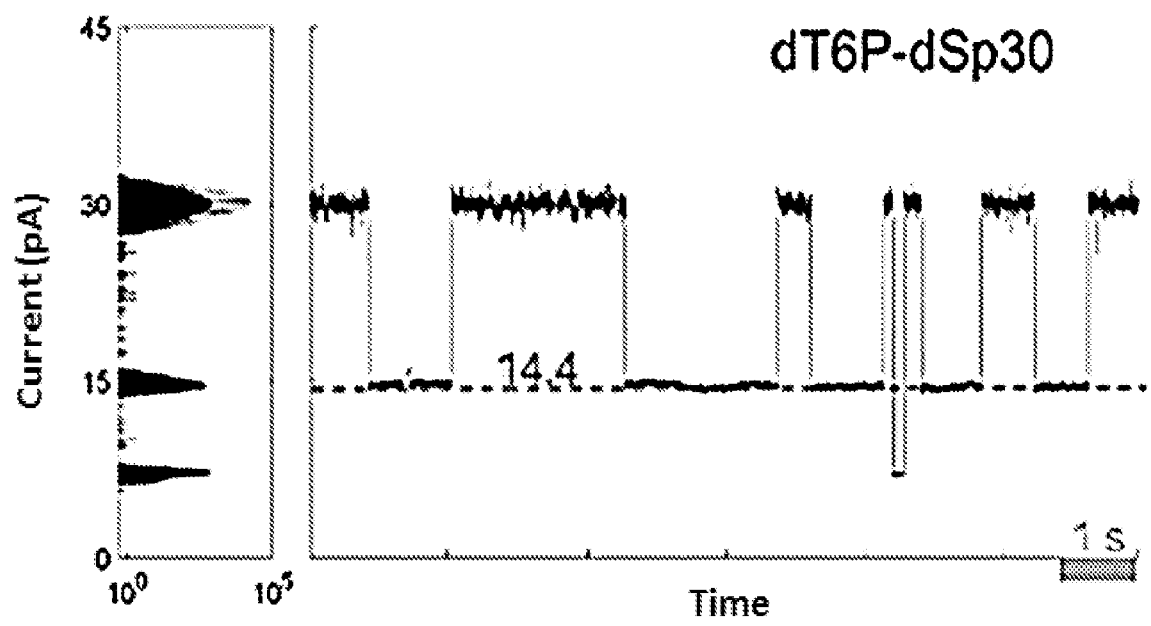
Figure 15A:
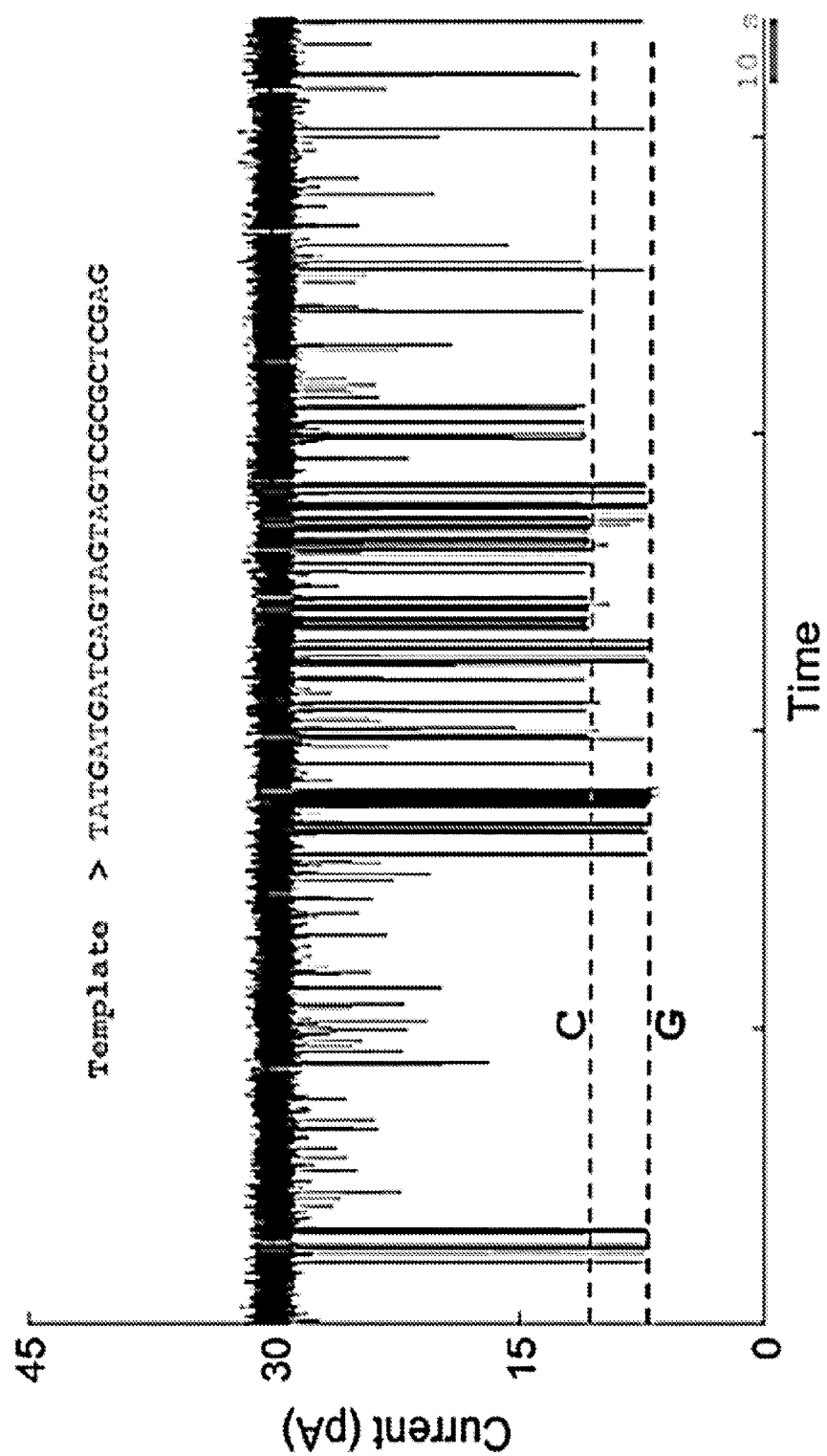
FIGS. 15A-B show representative examples of real-time detection of numerous successive tagged nucleotide incorporations into a self-priming DNA hairpin template catalyzed by nanopore-bound polymerase on the Genia chip. Two base captures of tagged C and G nucleotides with standard A and T nucleotides, are shown in FIG. 15A. Part of the template sequence (SEQ ID NO: 6), with homopolymers grouped into a single base, is shown in red. The only captures observed in the trace match the expected levels for dG6P-T30 ("T30" disclosed as SEQ ID NO: 2) and dC6P-dSp3. Four base sequencing is shown in FIG. 15B. Events were categorized by manually assigning current blockade signatures to their respective tag capture boxes. Of the 12 bases sequenced, 85% match the template strand (SEQ ID NO: 7), with one incorrectly identified base, and one deletion.
Figure 15B:
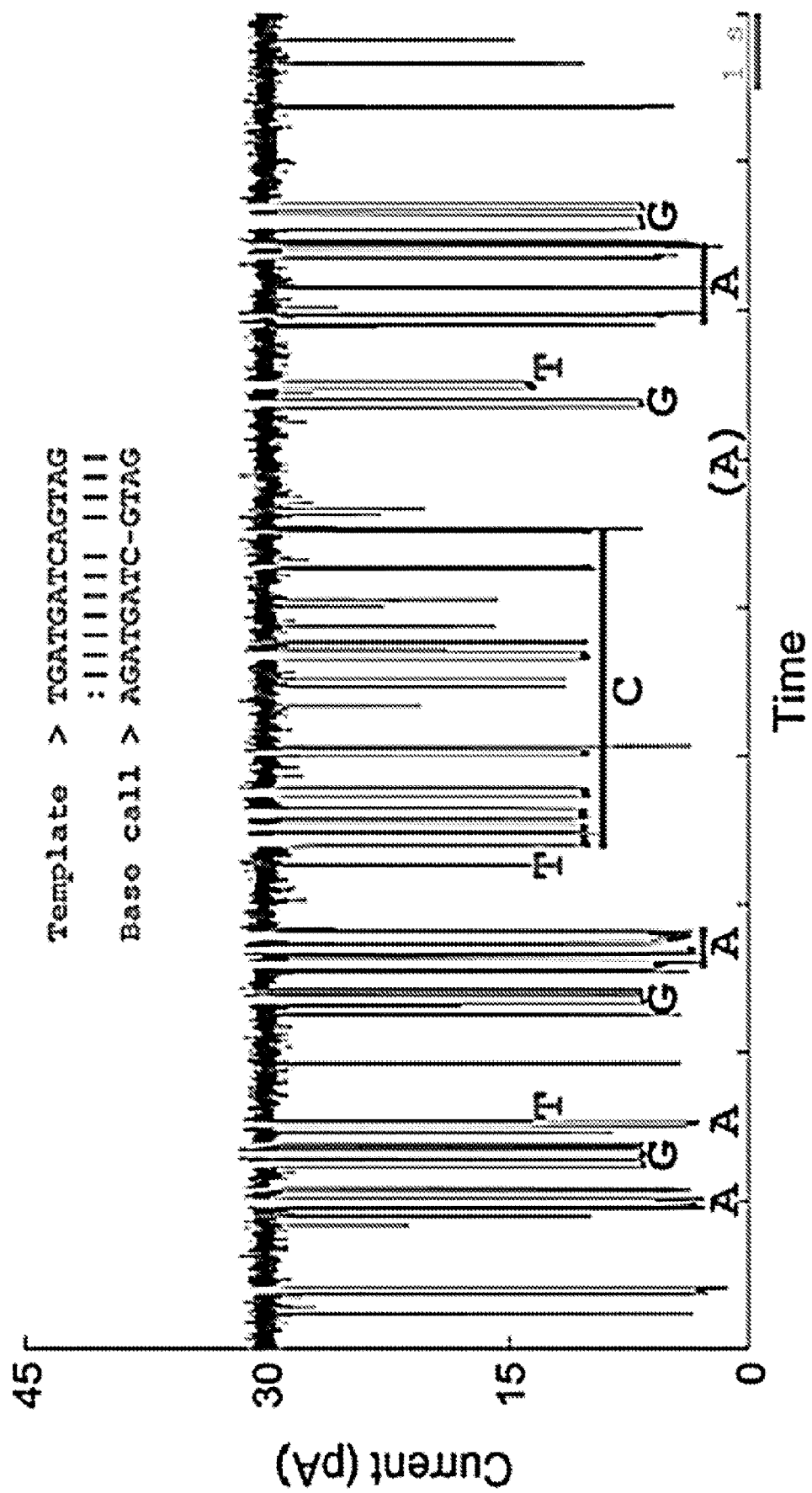

As a conservative classification method, we have identified the ternary complex capture (TCC) events as all events clustered inside the tag capture box defined by a mean dwell time interval of $10^{-2}$ to $10^{+1}$ seconds and a normalized current blockade (or residual current) region bounded by the $1^{st}$ and $3^{rd}$ quartile median values (lower/upper bounds) of the normalized current blockage boxplots—for a particular tagged nucleotide—respectively (FIGS. 14A-B).

What is claimed is:

1. A method of encoding information through synthesis of a DNA strand comprising
providing an encoding unit comprising a DNA polymerase, a single-stranded DNA (ssDNA) and a nanopore, wherein the DNA polymerase is conjugated to the nanopore,
providing a lipid bilayer having on opposite sides a cis and a trans reservoir each having a different buffer composition, wherein the nanopore is within the lipid bilayer and the DNA polymerase and the ssDNA are in the cis reservoir,
introducing into the cis reservoir a specific nucleotide corresponding to an encoding scheme for information storage in synthesized DNA, and
applying a voltage across the lipid bilayer via an electrode wherein the electrode can modulate the voltage across the lipid bilayer,
wherein catalytic ions $Mg^{2+}$ or $Co^{2+}$ are injected to the cis side from the trans side, thereby activating the DNA polymerase to catalyze addition of the specific nucleotide to the single stranded DNA during DNA synthesis, and
repeating catalytic addition to create synthesized DNA wherein the information is encoded and stored in the synthesized DNA.

2. The method of claim 1, wherein the DNA polymerase is a template dependent or independent DNA polymerase.

3. The method of claim 2, wherein the DNA polymerase is a φ29 DNA polymerase or a terminal deoxynucleotidyl transferase.

4. The method of claim 1, wherein the ssDNA is immobilized to the nanopore.

5. The method of claim 1, wherein the ssDNA is a template or an initiator for DNA synthesis.

6. The method of claim 1, wherein the nanopore is a protein membrane channel.

7. The method of claim 6, wherein the protein membrane channel comprises αHL, MspA, or φ29 connector.

8. The method of claim 1, wherein the cis reservoir contains non-catalytic buffer comprising non-catalytic ion $Ca^{2+}$ that prevents base addition during DNA synthesis, and wherein the trans reservoir contains catalytic buffer comprising catalytic ion $Mg^{2+}$ or $Co^{2+}$ that promotes base addition during DNA synthesis.

9. The method of claim 1, further comprising providing nucleotide bases to the cis reservoir and turning on the voltage such that catalytic ions $Mg^{2+}$ or $Co^{2+}$ are injected to the cis side from the trans side, thereby activating the enzyme that catalyzes the addition of the nucleotide bases during DNA synthesis.

10. The method of claim 1, wherein the nucleotide base can be added as a single base or a homopolymer run during DNA synthesis.

11. The method of claim 1, further comprising turning off the voltage, flushing the cis reservoir with fresh non-catalytic buffer and removing any nucleotide bases and catalytic ions.

12. The method of claim 1, wherein the method is capable of single molecule measurement.

13. The method of claim 1, wherein the method records voltage polarity applied across the lipid bilayer over time by encoding this information into a complement strand of DNA during DNA synthesis.

14. The method of claim 13, wherein the information is stored in the complement strand in the form of regions of bases either containing or lacking cytosine bases at the sites which complement the inosine bases of the template strand, which translates to the "1" or "0" state of a single bit of information.

15. The method of claim 1, wherein the ssDNA is immobilized to the nanopore within the cis reservoir.

16. The method of claim 1, wherein the 5' end of the ssDNA is immobilized to the nanopore.

17. The method of claim 1, wherein the 5' end of the ssDNA is immobilized to the nanopore within the cis reservoir.

18. A method of DNA synthesis comprising applying a voltage across a lipid bilayer having one or more encoding units associated therewith, wherein each encoding unit comprises a DNA polymerase an enzyme, a single-stranded DNA (ssDNA) and a nanopore, wherein the lipid bilayer has on opposite sides a cis and a trans reservoir each having a different buffer composition, wherein the trans reservoir comprises catalytic ions, wherein the nanopore is within the lipid bilayer and the DNA polymerase enzyme and the ssDNA are conjugated to the nanopore and are in the cis reservoir, and wherein the catalytic ions move from the trans reservoir to the cis reservoir in response to the voltage and the DNA polymerase enzyme is activated and catalyzes DNA synthesis in the presence of a nucleotide response to the voltage.

19. The method of claim 18, wherein the cis reservoir further comprises nucleotide bases.

20. The method of claim 18, wherein the voltage is applied via an electrode that modulates the voltage across the lipid bilayer.

21. The method of claim 18, wherein the ssDNA is linear.

22. The method of claim 18 wherein the ssDNA is a circular single-stranded DNA.

* * * * *

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tttttttttt tttttttttt                                    30

<210> SEQ ID NO 3
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (10)..(10)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (20)..(20)
<223> OTHER INFORMATION: Inosine
<220> FEATURE:
<221> NAME/KEY: modified_base
<222> LOCATION: (25)..(25)
<223> OTHER INFORMATION: Inosine
<220> FEATURE:
<221> NAME/KEY: modified_base
<222> LOCATION: (30)..(30)
<223> OTHER INFORMATION: Inosine
<220> FEATURE:
<221> NAME/KEY: modified_base
<222> LOCATION: (35)..(35)
<223> OTHER INFORMATION: Inosine
<220> FEATURE:
<221> NAME/KEY: modified_base
<222> LOCATION: (40)..(40)
<223> OTHER INFORMATION: Inosine
<220> FEATURE:
<221> NAME/KEY: modified_base
```

```
<222> LOCATION: (45)..(45)
<223> OTHER INFORMATION: Inosine
<220> FEATURE:
<221> NAME/KEY: modified_base
<222> LOCATION: (50)..(50)
<223> OTHER INFORMATION: Inosine
<220> FEATURE:
<221> NAME/KEY: modified_base
<222> LOCATION: (55)..(55)
<223> OTHER INFORMATION: Inosine
<220> FEATURE:
<221> NAME/KEY: modified_base
<222> LOCATION: (60)..(60)
<223> OTHER INFORMATION: Inosine

<400> SEQUENCE: 3
ctacnacttn caacnataan atctnccaan ctacnatcan taacncctan acttntcacn    60
aa                                                                  62

<210> SEQ ID NO 4
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttcgtgacaa gtctaggcgt tactgatcgt agcttggcag atcttatcgt tgcaagtcgt    60
ag                                                                  62

<210> SEQ ID NO 5
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gaacatttcg aagcttagcg atgcaagtcg ttgctataca gtgcttgcga tgatagattg    60
aagggatttg aaaggta                                                  77

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tatgatgatc agtagtagtc gcgctcgag                                     29

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgatgatcag tag                                                      13

<210> SEQ ID NO 8
```

-continued

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agatgatcgt ag                                                            12

<210> SEQ ID NO 9
<211> LENGTH: 720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Ser Trp Ser His Pro Gln Phe Glu Lys Gly Ala Glu Thr His
 1               5                  10                  15

Met Pro Arg Lys Met Tyr Ser Cys Asp Phe Glu Thr Thr Lys Val
            20                  25                  30

Glu Asp Cys Arg Val Trp Ala Tyr Gly Tyr Met Asn Ile Glu Asp His
        35                  40                  45

Ser Glu Tyr Lys Ile Gly Asn Ser Leu Asp Glu Phe Met Ala Trp Val
 50                  55                  60

Leu Lys Val Gln Ala Asp Leu Tyr Phe His Asn Leu Lys Phe Asp Gly
 65                  70                  75                  80

Ala Phe Ile Ile Asn Trp Leu Glu Arg Asn Gly Phe Lys Trp Ser Ala
                85                  90                  95

Asp Gly Leu Pro Asn Thr Tyr Asn Thr Ile Ile Ser Arg Met Gly Gln
           100                 105                 110

Trp Tyr Met Ile Asp Ile Cys Leu Gly Tyr Lys Gly Lys Arg Lys Ile
       115                  120                 125

His Thr Val Ile Tyr Asp Ser Leu Lys Lys Leu Pro Phe Pro Val Lys
   130                 135                 140

Lys Ile Ala Lys Asp Phe Lys Leu Thr Val Leu Lys Gly Asp Ile Asp
145                 150                 155                 160

Tyr His Lys Glu Arg Pro Val Gly Tyr Lys Ile Thr Pro Glu Glu Tyr
                165                 170                 175

Ala Tyr Ile Lys Asn Asp Ile Gln Ile Ile Ala Glu Ala Leu Leu Ile
            180                 185                 190

Gln Phe Lys Gln Gly Leu Asp Arg Met Thr Ala Gly Ser Asp Ser Leu
        195                 200                 205

Lys Gly Phe Lys Asp Ile Ile Thr Thr Lys Lys Phe Lys Lys Val Phe
    210                 215                 220

Pro Thr Leu Ser Leu Gly Leu Asp Lys Glu Val Arg Tyr Ala Tyr Arg
225                 230                 235                 240

Gly Gly Phe Thr Trp Leu Asn Asp Arg Phe Lys Glu Lys Glu Ile Gly
                245                 250                 255

Glu Gly Met Val Phe Asp Val Asn Ser Leu Tyr Pro Ala Gln Met Tyr
            260                 265                 270

Ser Arg Leu Leu Pro Tyr Gly Glu Pro Ile Val Phe Glu Gly Lys Tyr
        275                 280                 285

Val Trp Asp Glu Asp Tyr Pro Leu His Ile Gln His Ile Arg Cys Glu
    290                 295                 300
```

-continued

```
Phe Glu Leu Lys Glu Gly Tyr Ile Pro Thr Ile Gln Ile Lys Arg Ser
305                 310                 315                 320

Arg Phe Tyr Lys Gly Asn Glu Tyr Leu Lys Ser Ser Gly Gly Glu Ile
                325                 330                 335

Ala Asp Leu Trp Leu Ser Asn Val Asp Leu Glu Leu Met Lys Glu His
            340                 345                 350

Tyr Asp Leu Tyr Asn Val Glu Tyr Ile Ser Gly Leu Lys Phe Lys Ala
        355                 360                 365

Thr Thr Gly Leu Phe Lys Asp Phe Ile Asp Lys Trp Thr Tyr Ile Lys
    370                 375                 380

Thr Thr Ser Glu Gly Ala Ile Lys Gln Leu Ala Lys Leu Met Leu Asn
385                 390                 395                 400

Ser Leu Tyr Gly Lys Phe Ala Ser Asn Pro Asp Val Thr Gly Lys Val
                405                 410                 415

Pro Tyr Leu Lys Glu Asn Gly Ala Leu Gly Phe Arg Leu Gly Glu Glu
            420                 425                 430

Glu Thr Lys Asp Pro Val Tyr Thr Pro Met Gly Val Phe Ile Thr Ala
        435                 440                 445

Trp Ala Arg Tyr Thr Thr Ile Thr Ala Ala Gln Ala Cys Tyr Asp Arg
    450                 455                 460

Ile Ile Tyr Cys Asp Thr Asp Ser Ile His Leu Thr Gly Thr Glu Ile
465                 470                 475                 480

Pro Asp Val Ile Lys Asp Ile Val Asp Pro Lys Lys Leu Gly Tyr Trp
                485                 490                 495

Ala His Glu Ser Thr Phe Lys Arg Ala Lys Tyr Leu Arg Gln Lys Thr
            500                 505                 510

Tyr Ile Gln Asp Ile Tyr Met Lys Glu Val Asp Gly Lys Leu Val Glu
        515                 520                 525

Gly Ser Pro Asp Asp Tyr Thr Asp Ile Lys Phe Ser Val Lys Cys Ala
    530                 535                 540

Gly Met Thr Asp Lys Ile Lys Lys Glu Val Thr Phe Glu Asn Phe Lys
545                 550                 555                 560

Val Gly Phe Ser Arg Lys Met Lys Pro Lys Pro Val Gln Val Pro Gly
                565                 570                 575

Gly Val Val Leu Val Asp Asp Thr Phe Thr Ile Lys Gly Ser Gly Asp
            580                 585                 590

Tyr Asp Ile Pro Thr Thr Glu Asn Leu Tyr Phe Gln Gly Ala Met Val
        595                 600                 605

Asp Thr Leu Ser Gly Leu Ser Ser Glu Gln Gly Gln Ser Gly Asp Met
    610                 615                 620

Thr Ile Glu Glu Asp Ser Ala Thr His Ile Lys Phe Ser Lys Arg Asp
625                 630                 635                 640

Glu Asp Gly Lys Glu Leu Ala Gly Ala Thr Met Glu Leu Arg Asp Ser
                645                 650                 655

Ser Gly Lys Thr Ile Ser Thr Trp Ile Ser Asp Gly Gln Val Lys Asp
            660                 665                 670

Phe Tyr Leu Tyr Pro Gly Lys Tyr Thr Phe Val Glu Thr Ala Ala Pro
        675                 680                 685

Asp Gly Tyr Glu Val Ala Thr Ala Ile Thr Phe Thr Val Asn Glu Gln
    690                 695                 700

Gly Gln Val Thr Val Asn Gly Lys Ala Thr Lys Gly Asp Ala His Ile
705                 710                 715                 720
```

<210> SEQ ID NO 10
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Glu Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn Gly Ser Ser Gly Ser Ser Gly Gly
    290                 295                 300

Ala His Ile Val Met Val Asp Ala Tyr Lys Pro Thr Lys Lys Gly His
305                 310                 315                 320

His His His His
            325